United States Patent
Anavi-Goffer et al.

(10) Patent No.: US 10,016,373 B2
(45) Date of Patent: *Jul. 10, 2018

(54) CB2 RECEPTOR LIGANDS FOR THE TREATMENT OF PSYCHIATRIC DISORDERS

(71) Applicant: ARIEL—UNIVERSITY RESEARCH AND DEVELOPMENT COMPANY, LTD., Ariel (IL)

(72) Inventors: Sharon Anavi-Goffer, Ashod (IL); Juerg Gertsch, Schaffhausen (CH)

(73) Assignee: Sharon Anavi-Goffer, Oranit (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/336,114

(22) Filed: Oct. 27, 2016

(65) Prior Publication Data

US 2017/0042832 A1 Feb. 16, 2017

Related U.S. Application Data

(63) Continuation of application No. 14/785,086, filed as application No. PCT/IL2014/050364 on Apr. 16, 2014, now Pat. No. 9,486,419.

(Continued)

(51) Int. Cl.
| | |
|---|---|
| *A61K 31/135* | (2006.01) |
| *A61K 31/085* | (2006.01) |
| *C07C 43/23* | (2006.01) |
| *A61K 31/138* | (2006.01) |
| *A61K 31/40* | (2006.01) |
| *A61K 31/4535* | (2006.01) |
| *A61K 31/55* | (2006.01) |

(52) U.S. Cl.
CPC .......... *A61K 31/085* (2013.01); *A61K 31/138* (2013.01); *A61K 31/40* (2013.01); *A61K 31/4535* (2013.01); *A61K 31/55* (2013.01); *C07C 43/23* (2013.01)

(58) Field of Classification Search
CPC ...... A61K 31/85; A61K 31/138; A61K 31/55; A61K 31/40; A61K 31/4535; C07C 43/23
USPC ........................................................ 514/651
See application file for complete search history.

(56) References Cited

U.S. PATENT DOCUMENTS

| | | |
|---|---|---|
| 6,864,291 B1 | 3/2005 | Fride et al. |
| 8,604,087 B2 | 12/2013 | Kim et al. |

(Continued)

FOREIGN PATENT DOCUMENTS

| | | |
|---|---|---|
| KR | 10-20110073653 | 6/2011 |
| WO | 99/00346 A1 | 1/1999 |

(Continued)

OTHER PUBLICATIONS

Atwood et al. (2010) "CB2: a cannabinoid receptor with an identity crisis," Br J Pharmacol 160(3): 467-479.

(Continued)

*Primary Examiner* — Taylor V Oh
(74) *Attorney, Agent, or Firm* — Greenberg Traurig, LLP

(57) ABSTRACT

The present invention provides cannabinoid type 2 (CB2) receptor inverse agonists for treating or ameliorating psychiatric disorders. The present invention further provides pharmaceutical compositions comprising 4'-O-methylhonokiol for treating Attention Deficit Hyperactivity Disorder (ADHD) and Tourette's syndrome.

12 Claims, 17 Drawing Sheets

Related U.S. Application Data

(60) Provisional application No. 61/812,742, filed on Apr. 17, 2013.

(56) References Cited

U.S. PATENT DOCUMENTS

| | | | |
|---|---|---|---|
| 9,486,419 B2* | 11/2016 | Anavi-Goffer | A61K 31/085 |
| 2006/0172019 A1 | 8/2006 | Ralston et al. | |
| 2007/0191340 A1 | 8/2007 | Zindell et al. | |
| 2008/0194656 A1 | 8/2008 | Berwaer et al. | |
| 2008/0234237 A1 | 9/2008 | Maddaford et al. | |
| 2016/0089349 A1 | 3/2016 | Anavi-Goffer et al. | |

FOREIGN PATENT DOCUMENTS

| | | |
|---|---|---|
| WO | 00/40532 A2 | 7/2000 |
| WO | 2002003975 | 1/2002 |
| WO | 2007138431 | 12/2007 |
| WO | 2010/102560 A2 | 8/2012 |
| WO | 2012/102562 | 8/2012 |
| WO | 2013028480 | 2/2013 |

OTHER PUBLICATIONS

Fergusson et al. (2008) "Cannabis use and adult ADHD symptoms," Drug Alcohol Depend 95(1-2): 90-96.

Gadzicki et al. (2004) Tourette Syndrome is not Caused by Mutations in the Central Cannabinoid Receptor (CNR1) Gene, Am J Med Genet B Neuropsychiatr Genet 127B(1): 97-103.

Gertsch et al. (2012) "Methylhonokiol attenuates neuroinflammation: a role for cannabinoid receptors?," J Neuroinflammation 9: 135 (5 pages).

Hemming et al. (1993) "Effective treatment of Tourette's syndrome with marijuana," J Psychopharmacol 7(4): 389-391.

Josselyn et al. (1998) "Preclinical Behavioral Approaches to the Identification and Study of Antipsychotic Drug action and Schizophrenia," In: In Vivo Neuromethods; Boulton AA, Baker GB and Bateson AN (editors). vol. 32 of the series Neuromethods, pp. 177-225; Humana Press, Totowa.

Kumar et al. (2013) "Identification of raloxifene as a novel CB2 inverse agonist," Biochem Biophys Res Commun 435(1): 76-81.

Kuribara et al ,Honokiol, aPutative Anxiolytic agent extracted from Magnolia Bark, has no Diazepam-like Side-effects in Mice, Journal of Pharmacy and Pharmacology, 1999, 51:p. 97-100.

Lafenetre et al. (2009) "Bidirectional regulation of novelty-induced behavioral inhibition by the endocannabinoid system," Neuropharmacology 57(7-8): 715-721.

Lee et al. (2012) "Inhibitory effect of 4-O-methylhonokiol on lipopolysaccharide-induced neuroinflammation, amyloidogenesis and memory impairment via inhibition of nuclear factor-kappaB in vitro and in vivo models," J Neuroinflammation 9: 35 (19 pages).

McNaught et al. (2011) "Advances in understanding and treatment of Tourette syndrome," Nat Rev Neurol 7(12): 667-676.

Muller-Vahl et al. (1998) "Cannabinoids: possible role in pathophysiology and therapy of Gilles de la Tourette syndrome," Acta Psychiatr Scand 98(6): 502-506.

Muller-Vahl et al. (2003) "Delta 9-Tetrahydrocannabinol (THC) is Effective in the Treatment of Tics in Tourette Syndrome: A 6-Week Randomized Trial," J Clin Psychiatry 64(4): 459-465.

Muller-Vahl et al. (2003) "Treatment of Tourette Syndrome with Delta-9-Tetrahydrocannabinol (Delta 9-THC): No Influence on Neuropsychological Performance," Neuropsychopharmacology 28(2): 384-388.

Onaivi (2009) "Cannabinoid receptors in brain: pharmacogenetics, neuropharmacology, neurotoxicology, and potential therapeutic applications," Int Rev Neurobiol 88: 335-369.

Prather et al. (2013) "CBI and CB2 receptors are novel molecular targets for Tamoxifen and 40H-Tamoxifen," Biochem Biophys Res Commun 441(2): 339-343.

Sandyk et al. (1988) "Marijuana and Tourette's Syndrome," J Clin Psychopharmacol 8(6): 444-445.

Sandyk et al. (1987) "Clomiphene citrate in Tourette's syndrome," Postgrad Med J 63(740): 510-511.

Schuehly et al. (2011) "Mechanisms of Osteoclastogenesis Inhibition by a Novel Class of Biphenyl-Type Cannabinoid CB(2) Receptor Inverse Agonists," Chem Biol 18(8): 1053-1064.

Stratton et al. (2012) "Cannabinoid Receptors Provide New Targets in Battling Anxiety," Biochem Pharmacal 1: 7 (3 pages).

International Search Report, PCT/IL2014/050364, dated Aug. 3, 2014.

International Preliminary Report on Patentability, PCT/IL2014/050364, dated Oct. 20, 2015.

* cited by examiner

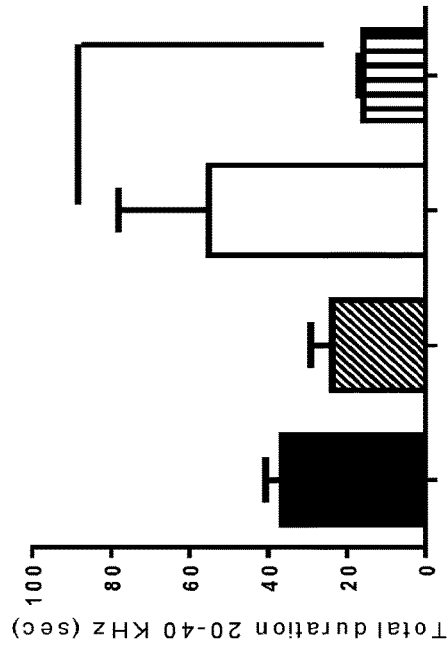
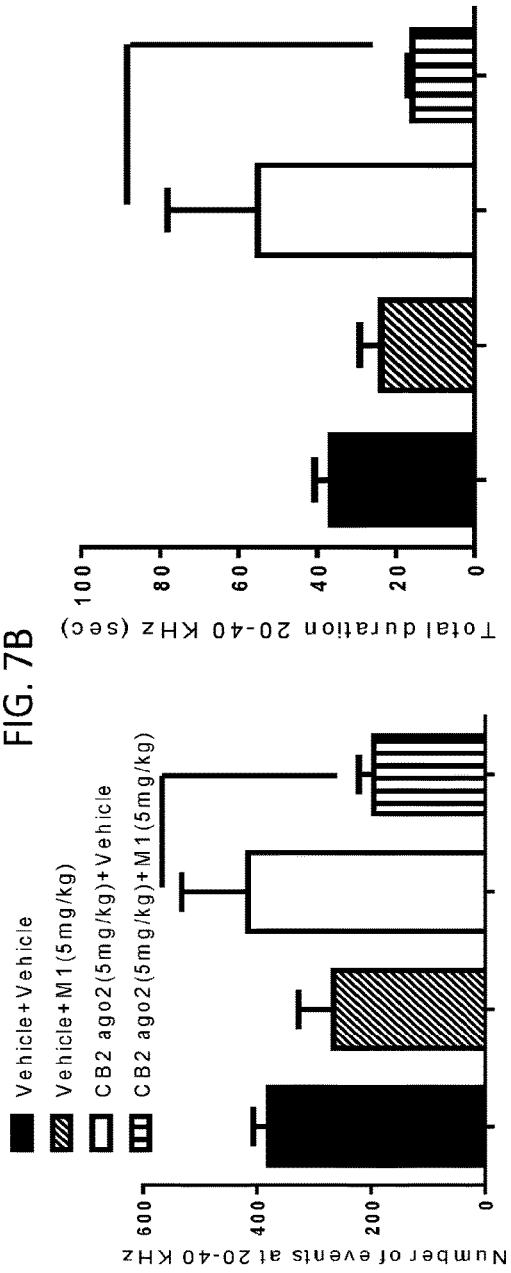
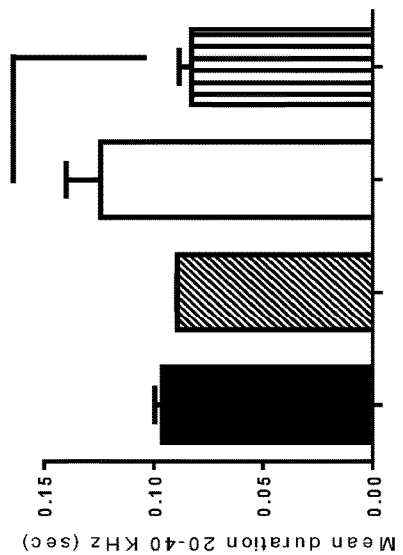
FIG. 7A
FIG. 7B
FIG. 7C

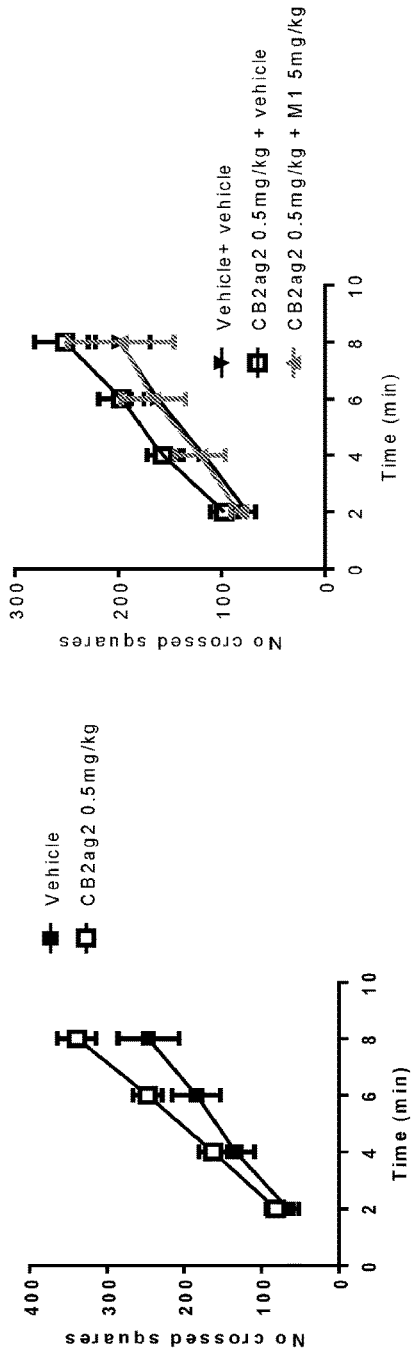
FIG. 11A
FIG. 11B
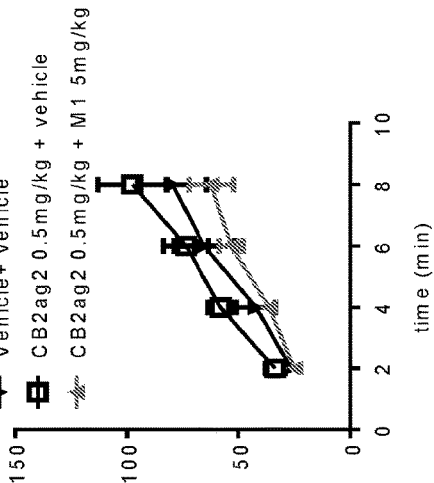
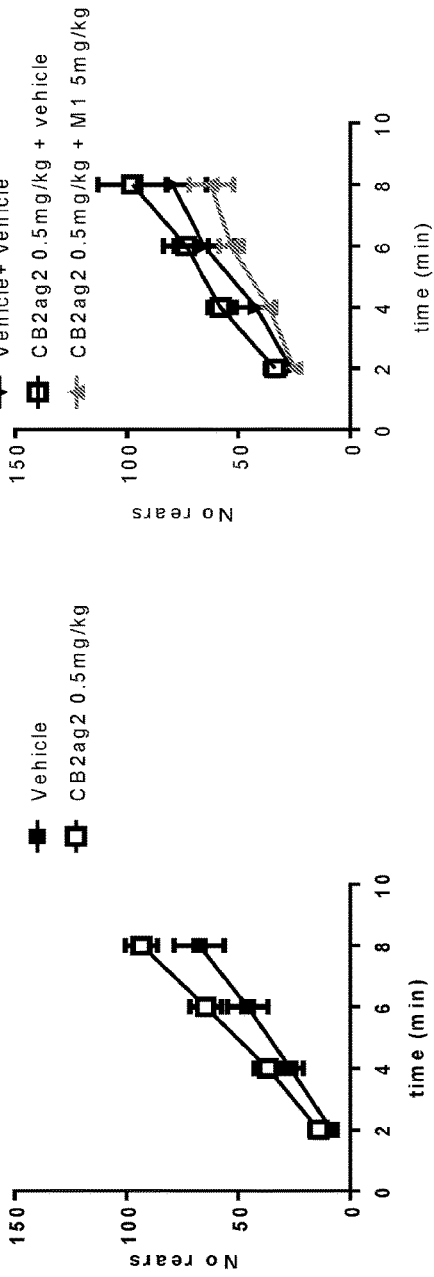
FIG. 11C
FIG. 11D

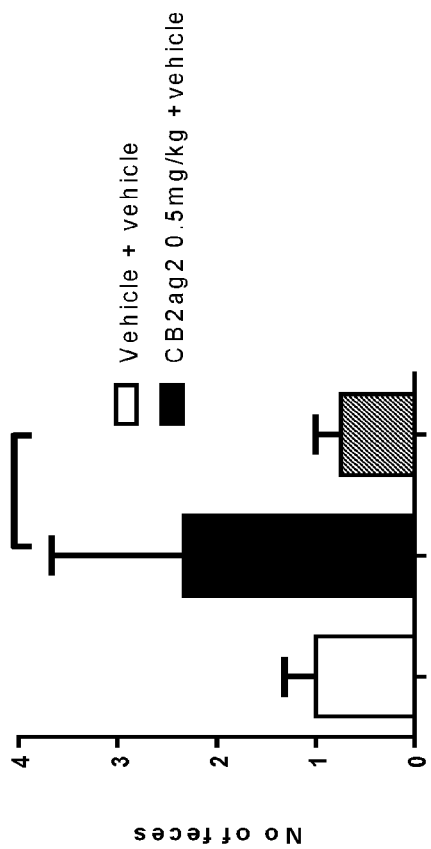
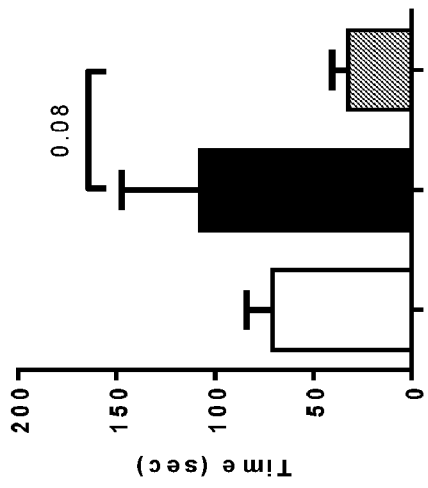
FIG. 13A
FIG. 13B

CB2 RECEPTOR LIGANDS FOR THE TREATMENT OF PSYCHIATRIC DISORDERS

CROSS-REFERENCE

This application is a continuation application of U.S. patent application Ser. No. 14/785,086, filed Oct. 16, 2015, which is a § 371 application of International Application No. PCT/IL14/050364, filed Apr. 16, 2014, which claims priority to U.S. Provisional Patent Application No. 61/812,742, filed on Apr. 17, 2013, the entire contents of which are incorporated by reference in their entirety.

FIELD OF THE INVENTION

The present invention relates to cannabinoid type 2 (CB2) receptor ligands for treating or ameliorating psychiatric disorders. The present invention further relates to pharmaceutical compositions comprising a CB2 receptor inverse agonist 4'-O-methylhonokiol for treating Attention Deficit Hyperactivity Disorder (ADHD) and tic disorders.

BACKGROUND OF THE INVENTION

Cannabinoids are compounds found in *Cannabis sativa* (also know as marijuana) with cannabinol, cannabidiol and $\Delta^9$-tetrahydrocannabinol ($\Delta^9$-THC) being the most representative molecules. The therapeutic usage of *Cannabis* can be dated back to ancient dynasties of China and includes applications for various illnesses ranging from lack of appetite, emesis, cramps, menstrual pain, spasticity to rheumatism. The long history of *Cannabis* use has led to the development of several pharmaceutical drugs. For example, Marinol and Cesamet which are based on $\Delta^9$-THC and its analogous nabilone, respectively, are used as anti-emetic and appetite stimulant. Despite of the clinical benefits, the therapeutic usage of *Cannabis* is limited by its psychoactive effects including hallucination, addiction and dependence.

The effects of $\Delta^9$-THC are mediated by at least two G-protein coupled receptors, CB1 and CB2 receptors. CB1 receptors are expressed primarily in the central nervous system, specifically in the cerebral cortex, hippocampus, basal ganglia and cerebellum. These receptors are also found in the reproductive system and in other peripheral tissues including that of the immune system, but to a lesser degree. CB1 receptors regulate the release of neurotransmitters from the pre-synaptic neurons and are believed to mediate most of the euphoric and other central nervous system effects of $\Delta^9$-THC.

CB2 receptors are widely expressed in different tissues, primarily in the immune system, with the greatest density in the spleen. The expression level of CB2 in the immune cells is about 10 to 100 times higher than CB1. Within the immune system, CB2 is found in various cell types, including B cells, NK cells, monocytes, microglial cells, neutrophils, T cells, dendritic cells and mast cells. CB2 selective ligands have been developed and tested for their effects in various inflammatory settings. The results have indicated that CB2 receptor modulators can be employed for the treatment of medical conditions having an inflammatory component.

In addition to inflammation, modulation of CB2 receptor activity has been shown to be involved in the pathophysiology of different diseases, including osteoporosis, atherosclerosis, chronic pain, and cancer.

CB2 receptors are largely absent in the central nervous system (CNS) of adult mammals under normal conditions. The expression of CB2 receptors in the fully matured brain is about 1.5% of the level in the spleen, and these receptors are present on neuronal cells, mainly in the cerebellum and in the brain stem. However, CB2 receptors appear to be upregulated in microglial cells and astrocytes under selected neuroinflammatory stimulation.

4'-O-methylhonokiol

Honokiol, magnolol and 4'-O-methylhonokiol belong to a class of neolignan biphenols. These compounds are isolated from the barks, seed cones, and leaves of trees belonging to the genus *Magnolia*. In China, Korea, and Japan extracts from the bark or seed cones of the *Magnolia* tree have been widely used in traditional medicine as analgesic and to treat anxiety and mood disorders. During the last decades, honoldol has been shown to be a pleotropic compound exhibiting not only analgesic, anxiolytic, and antidepressant effects, but also antiemetic, anti-inflammatory, antibacterial, anti-tumorigenic, antithrombotic, neuroprotective, neurotrophic, and serotonergic effects.

The biphenyl neolignan 4'-O-methylhonoldol (MH) isolated from *Magnolia grandiflora* L. seeds is a potent CB2 receptor ligand (Ki=50 nM), showing a unique inverse agonism and partial agonism via different pathways (cAMP and Ca2+, respectively) and potently inhibits osteoclastogenesis (Schuehly et al., Chem. & Biol. 18: 1053-1064, 2011). MH further attenuates memory impairment in presenilin 2 mutant mice through reduction of oxidative damage and inactivation of astrocytes and the ERK pathway. In a mouse model of Alzheimer's disease (AD), the orally administered MH has been shown to prevent amyloidogenesis and progression of AD by inhibiting neuroinflammation (Lee et al., J. Neuroinflamm. 9:35, 2012). It was postulated that MH may exert its beneficial effects in the AD mouse model via modulation of CB2 receptors expressed in microglial cells and astrocytes (Gertsch and Anavi-Goffer et al., J. Neuroinflamm. 9:135, 2012).

Psychiatric Disorders: ADHD/ADD, OCD and TS

Attention Deficit Hyperactivity Disorder (ADHD) which also includes Attention Deficit Disorder (ADD) is a common psychiatric disorder, estimated as affecting 3-9% of school-aged children and young people and 2% of adults worldwide. In addition, in 90% of Tourette's Syndrome (TS) children, the tics exist in conjunction with another disorder, most frequently with ADHD/ADD and/or with OCD.

The cause of most cases of ADHD is unknown but it is believed to involve interactions between genetic and environmental factors. Typically a number of genes are involved, many of which directly affect dopamine neurotransmission. Environmental factors are believed to play a lesser role. Certain cases have been related to previous infection of or trauma to the brain. Very low birth weight, premature birth and early adversity also increase the risk as do infections during pregnancy, at birth, and in early childhood. At least 30% of children with a traumatic brain injury later develop ADHD and about 5% of cases are due to brain damage.

ADHD/ADD is believed to be linked to sub-performance of the dopamine and norepinephrine functions in the brain. The 'dopamine theory' of the origin of ADHD/ADD therefore provides the basis for the most common pharmaceutical treatment using methylphenidate. Methylphenidate is a dopamine reuptake inhibitor and also a much weaker norepinephrine reuptake inhibitor, which increases the levels of these neurotransmitters in the brain. However, up to 30% of subjects suffering from ADHD/ADD do not respond to methylphenidate, suggesting that other mechanisms may also be important. Additionally, methylphenidate has been shown to produce side effects, including increased blood pressure, cardiac arrhythmia, loss of appetite, insomnia and psychosis.

Other known classes of drugs for treatment of ADHD/ADD include the noradrenalin reuptake inhibitor atomoxetine that may increase obsessive behavior and blood pressure, and amphetamines that are known to be addictive.

Obsessive Compulsive Disorder (OCD), a type of anxiety disorder, is a potentially disabling illness that traps sufferers in endless cycles of repetitive thoughts and behaviors. Subjects suffering from OCD are plagued by recurring, distressing and uncontrollable thoughts, fears, or images (obsessions). The resulting anxiety leads to an urgent need to perform certain rituals or routines (compulsions). The compulsions are performed in an attempt to prevent or get rid of the obsessive thoughts. Although the compulsions may temporarily alleviate anxiety, the person must perform the compulsions again when the obsessive thoughts return. This OCD cycle can progress to the point of taking up hours of the person's day and significantly interfering with normal activities.

OCD has been linked to abnormalities with the neurotransmitter serotonin, although it could be either a cause or an effect of these abnormalities. It is hypothesized that the serotonin receptors of OCD sufferers may be relatively understimulated. This suggestion is consistent with the observation that many OCD patients benefit from the use of selective serotonin reuptake inhibitors (SSRIs), a class of antidepressant medications that allow for more serotonin to be readily available to other nerve cells.

Tourette's syndrome (TS) is an inherited neuropsychiatric disorder with onset in childhood, characterized by multiple physical (motor) tics and at least one vocal (phonic) tic. Between 0.4% and 3.8% of children ages 5 to 18 may have TS; the prevalence of other tic disorders in school-age children is higher, with the more common tics of eye blinking, coughing, throat clearing, sniffing, and facial movements. Extreme TS in adulthood is a rarity, and Tourette's does not adversely affect intelligence or life expectancy.

The exact cause of Tourette's syndrome is unknown but it is well established that both genetic and environmental factors are involved. The medication with the most proven efficacy in treating tics includes typical and atypical neuroleptics including risperidone (Risperdal®), which can have long-term and short-term adverse effects. The antihypertensive agents clonidine and guanfacine are also used to treat tics showing variable efficacy but a lower side effect profile than the neuroleptics. Stimulants and other medications may be useful in treating ADHD when it co-occurs with tic disorders. Drugs from several other classes of medications can be used when stimulant trials fail, including atomoxetine and tricyclic antidepressants. SSRIs may be prescribed when a Tourette's patient also has symptoms of OCD.

U.S. Patent Application Publication No. 2006/0172019 discloses cannabinoid (CB) receptor inverse agonists and neutral antagonists, and especially CB1 and CB2 inverse agonists and neutral antagonists, such as certain pyrazole compounds, and their use in the inhibition of osteoclasts and/or in the inhibition of bone resorption. U.S. 2006/0172019 further discloses use of CB1 and CB2 inverse agonists and neutral antagonists in treating bone disorders such as osteoporosis, cancer associated bone disorders, and Paget's disease of bone.

U.S. Patent Application Publication No. 2007/0191340 discloses compounds which bind to and are agonists, antagonists or inverse agonists of the CB2 receptor. U.S. 2007/0191340 further discloses methods and pharmaceutical compositions for treating inflammation by way of administration of these compounds as well as methods for treating pain by way of administration of a subset of these compounds, i.e., CB2 agonists.

U.S. Patent Application Publication No. 2008/0194656 discloses benzotriazole derivatives which are potent CB1 modulators, known as antagonists or inverse agonists, useful in the treatment of obesity, psychiatric and neurological disorders.

U.S. Pat. No. 6,864,291 discloses novel pharmaceutical compositions comprising as the active ingredient 4-phenyl pinene derivatives which are specific for the peripheral cannabinoid receptors, including the compound designated HU-308. In particular, the compounds bind efficiently to CB2 but do not bind to CB1. The compounds show no activity in behavioral tests in mice which together have been shown to be specific for tetrahydrocannabinol (THC)-type activity.

U.S. Pat. No. 8,604,087 discloses a composition for treating or preventing amyloid-related disease which includes 4-O-methylhonokiol as an active ingredient. Among the diseases, Alzheimer's disease, cognitive disorder, defective memory, and amyloidosis are listed.

WO 2012/102562 discloses compositions containing a methylhonokiol derivative to suppress beta-amyloid aggregation, beta-secretase activation, and neural cell apoptosis. WO 2012/102562 further discloses pharmaceutical compositions and food compositions for preventing or treating dementia which contain a methylhonokiol derivative.

WO 2012/102560 discloses a 4-O-methylhonokiol derivative having anti-inflammation activity by restraining activation of cyclooxygenase-2, thereby capable of being used for treating various inflammations.

There is an unmet need for improved methods for treating psychiatric disorders including ADHD, tic disorders and/or OCD, which methods show higher curability and have fewer or no side effects.

SUMMARY OF THE INVENTION

The present invention provides cannabinoid type 2 (CB2) receptor ligands which are optionally CB2 receptor inverse agonists or mixed-type agonists for the treatment of psychiatric disorders, including but not limited to, Attention Deficit Hyperactivity Disorder/Attention Deficit Disorder (ADHD/ADD), hyperactivity, tic disorders including Tourette's Syndrome (TS), and/or Obsessive Compulsive Disorder (OCD).

The present invention is based in part on the unexpected findings that postnatal exposure to selective agonists for CB2 receptors induced behavioral symptoms characteristic of ADHD, OCD and/or TS in a murine model. It is now disclosed that administration of selective CB2 receptor agonists: beta-caryophyllene or [(1R,2R,5R)-2-[2,6-dimethoxy-4-(2-methyloctan-2-yl)phenyl]-7,7-dimethyl-4-bicyclo[3.1.1]hept-3-enyl]methanol known as HU-308, to mice at postnatal age of three to fifteen days increased hyperactive behaviors such as ambulation and rearing activities in these mice immediately after treatment, and these activities lasted weeks and even months thereafter. Similarly, administration of beta-caryophyllene to mice at postnatal age of three to fifteen days increased the duration and frequency of grooming activity as well as inattention symptoms in the mice which were monitored a few weeks after treatment. These increased ambulation, rearing and grooming activities as well as the inattention symptoms are characteristic of hyperactivity behavior, thus representing ADHD-like and OCD-like behaviors.

It is further disclosed that administration of the selective CB2 receptor agonists beta-caryophyllene or HU-308 to mice pups at the age of three to fifteen days induced vocal and motor tics which resemble Tourette's syndrome-like behavior or other tic disorder-like behavior.

The present inventors show for the first time that selective CB2 receptor inverse agonists, and specifically 4'-O-methylhonokiol (also designated herein below M1), were able to reduce and even reverse the ADHD-like, the OCD-like and/or TS-like behavior. Such curative effects of the CB2 receptor inverse agonist M1 were observed in mice subjected to M1 treatment at earlier ages, namely at the age of three to six weeks, which correspond to childhood to teenage of a human subject. Moreover, the CB2 receptor inverse agonist M1 was also efficient in reversing the hyperactivity behavior and the tics in mice at the age of three to six months which correspond to adulthood of a human subject.

According to one aspect, the present invention provides a method for treating a psychiatric disorder comprising administering to a subject in need of such treatment a pharmaceutical composition comprising a therapeutically effective amount of a CB2 receptor inverse agonist of general formula I:

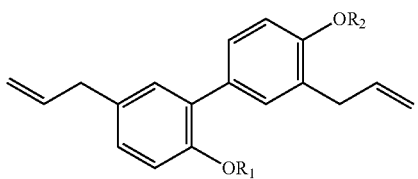

or a salt thereof and a pharmaceutically acceptable carrier, wherein $R_1$ and $R_2$ are each independently selected from the group consisting of hydrogen, unsubstituted or substituted $C_1$-$C_8$ alkyl, and unsubstituted or substituted $C_3$-$C_8$ cycloalkyl, and wherein the psychiatric disorder is selected from the group consisting of Attention Deficit Hyperactivity Disorder/Attention Deficit Disorder (ADHD/ADD), hyperactivity, a tic disorder, and a combination thereof. Each possibility is a separate embodiment of the invention.

According to a certain embodiment, $R_1$ is hydrogen and $R_2$ is methyl, and the CB2 receptor inverse agonist is thus 4'-O-Methylhonokiol designated throughout the specification M1 or MH which is known as a CB2 receptor inverse agonist/mixed-type agonist.

According to another embodiment, $R_1$ is hydrogen and $R_2$ is ethyl.

According to a further embodiment, $R_1$ and $R_2$ are each hydrogen, and the compound is honokiol.

According to additional embodiments, the tic disorder is selected from the group consisting of Tourette's syndrome (TS), chronic motor tic disorder, chronic vocal tic disorder, and transient tic disorder. Each possibility is a separate embodiment of the invention.

According to some embodiments, the pharmaceutical composition is formulated in a form selected from the group consisting of a solution, suspension, emulsion, powder, tablet, capsule, depot, transdermal patch, spray, and suppository. Each possibility is a separate embodiment of the invention.

According to additional embodiments, the pharmaceutical composition is administered by a route selected from the group consisting of oral, intravenous, intramuscular, intraperitoneal, subcutaneous, inhalation, transdermal, vaginal, and rectal administration route. Each possibility is a separate embodiment of the invention.

According to another aspect, the present invention provides a method for treating a psychiatric disorder comprising administering to a subject in need of such treatment a pharmaceutical composition comprising a therapeutically effective amount of a CB2 receptor inverse agonist and a pharmaceutically acceptable carrier, wherein the CB2 receptor inverse agonist is a selective estrogen receptor modulator (SERM), and wherein the psychiatric disorder is selected from the group consisting of ADHD/ADD, hyperactivity, OCD, and a combination thereof. Each possibility is a separate embodiment of the invention.

According to some embodiments, the SERM is selected from the group consisting of raloxifene, bazedoxifen, lasofoxifene, tamoxifen, afimoxifene, arzoxifene, ormeloxifene, toremifene, ospemifene, and analogs, derivatives or a combination thereof. According to additional embodiments, the SERM is selected from the group consisting of raloxifene, bazedoxifen, lasofoxifene and tamoxifen. Each possibility is a separate embodiment of the invention.

According to a certain embodiment, the psychiatric disorder is ADHD.

According to further embodiment, the pharmaceutical composition comprising the SERM is formulated in a form selected from the group consisting of a solution, suspension, emulsion, powder, tablet, capsule, depot, transdermal patch, spray, and suppository. Each possibility is a separate embodiment of the invention.

According to additional embodiments, the pharmaceutical composition comprising the SERM is administered by a route selected from the group consisting of oral, intravenous, intramuscular, intraperitoneal, subcutaneous, inhalation, transdermal, vaginal, and rectal administration route. Each possibility is a separate embodiment of the invention.

According to a further aspect, the present invention provides a pharmaceutical composition comprising a CB2 receptor inverse agonist of general formula I:

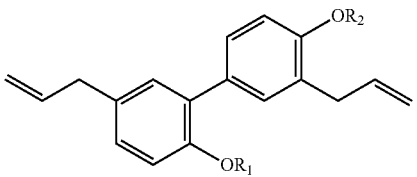

or salt thereof, for use in the treatment of a psychiatric disorder, wherein $R_1$ and $R_2$ are each independently selected from the group consisting of hydrogen, unsubstituted or substituted $C_1$-$C_8$ alkyl, and unsubstituted or substituted $C_3$-$C_8$ cycloalkyl, and wherein the psychiatric disorder is selected from the group consisting of Attention Deficit Hyperactivity Disorder/Attention Deficit Disorder (ADHD/ADD), hyperactivity, a tic disorder, and a combination thereof. Each possibility is a separate embodiment of the invention.

According to a certain embodiment, $R_1$ is hydrogen and $R_2$ is methyl, and the CB2 receptor inverse agonist is thus 4'-O-Methylhonokiol.

According to another aspect, the present invention provides a pharmaceutical composition comprising a CB2 receptor inverse agonist which is a selective estrogen receptor modulator (SERM) for use in the treatment of a psychiatric disorder selected from the group consisting of ADHD/ADD, hyperactivity, OCD, and a combination thereof.

These and other aspects and embodiments of the present invention will be better understood in relation to the figures, description, examples and claims that follow.

BRIEF DESCRIPTION OF THE FIGURES

FIG. 3A is a bar graph showing the effect of postnatal administration of CB2 agonist2 on the response to acoustic startle. FIG. 3B is a line graph showing the effect of postnatal administration of CB2 agonist2 on percent pre-pulse inhibition. FIGS. 3C and 3D are line graphs showing the effect of postnatal administration of HU-308 on percent pre-pulse inhibition in male (FIG. 3C) and female (FIG. 3D) mice.

FIGS. 7A-C are bar graphs showing the effect of treatment with M1 on CB2 agonist2-induced vocal tics/events in female mice at 20-40 kHz, after stress. FIG. 7A shows the effect of CB2 agonist2 and M1 on the number of vocal tics; FIG. 7B shows the effect of CB2 agonist2 and M1 on the total duration of vocal tics; FIG. 7C shows the effect of CB2 agonist2 and M1 on the mean duration of vocal tics.

FIG. 8A shows the effect of CB2 agonist2 and M1 on the number of vocal events.

FIG. 9A shows the effect of CB2 agonist2 and M1 on the total duration of vocal tics; FIG. 9B shows the effect of CB2 agonist2 and M1 on the mean duration of vocal tics.

FIG. 10A shows the effect of CB2 agonist2 and M1 on the number of vocal events; FIG. 10B shows the effect of CB2 agonist2 and M1 on the total duration of vocal events.

FIGS. 11A-D show the effect of CB2 agaonist2 and M1 on ambulation and rearing. FIGS. 11A and 11C are bar graphs showing the effect of 0.5 mg/kg CB2 agonist2 on ambulation (FIG. 11A) and rearing (FIG. 11C). FIGS. 11B and 11D are bar graphs showing that M1 reversed the effect of CB2 agonist2 on ambulation (FIG. 11B) and rearing (FIG. 11D).

FIGS. 13A-B are bar graphs showing that M1 reversed the effect of 0.5 mg/kg CB2 receptor agonist2 on grooming (FIG. 13A) and secretion of feces (FIG. 13B).

FIG. 16C shows that treatment with M1 had no effect on body weight at postnatal day 100 in mice treated with vehicle or CB2 agonist2.

DETAILED DESCRIPTION OF THE INVENTION

Figure 1A:
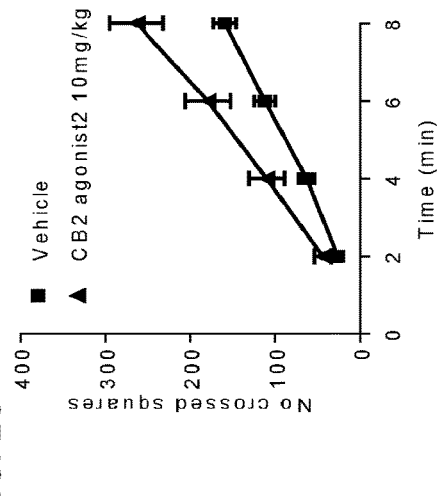
FIGS. 1A-D are line graphs showing the effect of postnatal administration of 5 mg/kg (FIGS. 1A-B) or 10 mg/kg (FIGS. 1C-D) of beta-caryophyllene also designated herein below CB2 agonist2 on ambulation (FIGS. 1A and 1C) and rearing (FIGS. 1B and 1D) using the open field test.

The present invention provides cannabinoid type 2 (CB2) receptor ligands, preferably acting as CB2 receptor inverse agonists, mixed-type agonists, antagonists, partial agonists, and/or CB2 receptor negative allosteric modulators for use in the treatment of Attention Deficit Hyperactivity Disorder (ADHD)/Attention Deficit Disorder (ADD), hyperactivity, a tic disorder including Tourette's Syndrome (TS), and/or Obsessive Compulsive Disorder (OCD).

Definitions

The term "CB2 receptor inverse agonist" refers to a ligand which binds to CB2 receptors in cells expressing CB2 receptors and increases cAMP production in these cells in the absence of any known CB2 receptor agonist. A typical assay for determining CB2 receptor inverse agonist utilizes CHO cells transfected with CB2 receptors and measuring cAMP production in the absence or presence of a test compound. or in the presence of forskolin (activated) (see, for example, Schuehly et al., ibid). It is to be understood that a CB2 receptor agonist inhibits cAMP production in cells expressing CB2 receptors. In the presence of a CB2 receptor agonist, the CB2 receptor inverse agonist reduces CB2 receptor agonistic activity, i.e., inhibition of cAMP production, and as such the CB2 receptor inverse agonist behaves as a CB2 receptor antagonist. Additionally or alternatively, the CB2 receptor inverse agonist may modulate or shift one or more activities mediated by the CB2 receptor, for example, intracellular $Ca^{2+}$ concentration. Thus, a CB2 receptor inverse agonist which increases cAMP production can exhibits full or partial agonistic effect on other CB2 receptor-mediated activities including, but not limited to, intracellular Ca2+ concentration, and as such it is referred to as a CB2 receptor mixed-type agonist. M1, for example, is known to be a CB2 receptor inverse agonist/mixed-type agonist due to its dual effects: increasing cAMP production and increasing intracellular Ca2+ concentration.

The term "inverse agonistic effect" means a partial or full inhibitory effect on CB2 receptor agonistic activity including, but not limited to, cAMP production, which effect reduces or inhibits the efficacy of any known CB2 receptor agonist and/or reduces the potency of any known CB2 receptor agonist. Typically, an inverse agonistic effect of a CB2 receptor ligand can be measured at a concentration of about 0.1 nM to about 10 µM.

The term "CB2 receptor partial agonist" means a ligand which binds to and activates the CB2 receptor but, relative to a full agonist, has only partial efficacy at the receptor. The partial agonist can be considered a ligand which displays both agonistic and antagonistic effects—when both ligands, a full agonist and a partial agonist are present, the partial agonist can act as an antagonist, competing with the full agonist for receptor occupancy and producing a net decrease in receptor activation observed with the full agonist alone.

The term "negative allosteric modulator" means a ligand which binds to a putative allosteric site/s of the CB2 receptor, distinct from the orthosteric sites (binding sites of the endogenous agonists), and increases cAMP production compared to cAMP production in its absence, thus reducing CB2 receptor agonistic activity.

The term "alkyl" is intended to include linear, branched, or cyclic hydrocarbon structures and combinations thereof. Examples of lower alkyl groups include, but are not limited to, methyl, ethyl, propyl, isopropyl, butyl, s- and t-butyl and the like. Cycloalkyl is a subset of alkyl and includes cyclic hydrocarbon groups of from 3 to 8 carbon atoms. Examples of cycloalkyl groups include cyclopropyl, cyclobutyl, cyclopentyl, cyclohexyl and the like.

The terms "substituted alkyl" and "substituted cycloalkyl" are intended to include substitution of a hydrogen with a halogen atom. The "halogen atom" means a fluorine atom, a chlorine atom, a bromine atom, or an iodine atom.

The terms "comprising", "including", "having" and grammatical variants thereof are to be taken as specifying the stated features, steps or components but do not preclude the addition of one or more additional features, steps, or components thereof.

As used herein, the indefinite articles "a" and "an" mean "at least one" or "one or more" unless the context clearly dictates otherwise.

As used herein, when a numerical value is preceded by the term "about", the term "about" is intended to indicate +/−10%.

The term "treating" includes curing and/or preventing a condition, curing and/or ameliorating symptoms of a condition.

The term "pharmaceutically acceptable" means approved by a regulatory agency of the U.S. Federal or a U.S. state government or listed in the U.S. Pharmacopeia or other generally recognized pharmacopeia for use in animals, and more particularly in humans. Herein, the phrase "pharmaceutically acceptable carrier" refers to an approved carrier or a diluent that does not cause significant irritation to a subject and does not abrogate the biological activity and properties of the active agent.

The term "therapeutically effective amount" means that amount of the compound being CB2 receptor inverse agonist and/or CB2 receptor mixed-type agonist and/or negative allosteric modulator which is sufficient to provide a beneficial effect to the subject to which the inverse agonist and/or mixed-type agonist and/or negative allosteric modulator is administered.

The term "carrier" refers to a diluent, adjuvant, excipient, or vehicle with which the active agent is administered. Herein the term "excipient" refers to an inert substance added to a pharmaceutical composition to further facilitate processes and administration of the active agent.

CB2 Receptor Inverse Agonists

The inventors have found that a pharmaceutical composition comprising M1 is effective in treating ADHD and/or OCD and/or TS in murine models.

4'-O-Methylhonokiol (2-(4-Methoxy-3-prop-2-enylphenyl)-4-prop-2-enylphenol; CAS number 68592-15-4, designated herein M1 or MH) is a CB2 receptor mixed-type agonist/inverse agonist, naturally found in the flowers of *Magnolia grandiflora* and *Magnolia virginiana*.

The present invention provides a method for the treatment of a psychiatric disorder comprising administering to a subject in need of such treatment a pharmaceutical composition comprising a therapeutically effective amount of a CB2 receptor inverse agonist of general formula I:

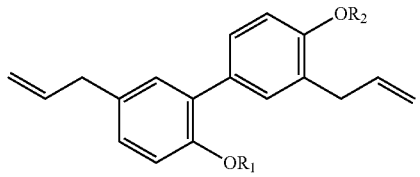

or a salt thereof and a pharmaceutically acceptable carrier, wherein $R_1$ and $R_2$ are each independently selected from the group consisting of hydrogen, unsubstituted or substituted $C_1$-$C_8$ alkyl, and unsubstituted or substituted $C_3$-$C_8$ cycloalkyl, and wherein the psychiatric disorder is selected from the group consisting of Attention Deficit Hyperactivity Disorder (ADHD)/Attention Deficit Disorder (ADD), hyperactivity, tic disorders, and a combination thereof. Each possibility is a separate embodiment of the invention.

The compounds represented by the general formula I may have various pharmaceutically acceptable salts due to the hydroxyl group, when present. Unless specified otherwise, the pharmaceutically acceptable salt includes all possible hydroxyl salts, including alkali metal salts such as sodium, potassium, and lithium, and alkaline earth metal salts such as calcium and magnesium salts. According to some embodiments, the pharmaceutically acceptable salt of the compound of general formula I includes sodium, potassium, or calcium. These salts may be prepared according to the methods known in the art.

According to a certain embodiment, the CB2 receptor inverse agonist is 4'-O-methylhonokiol (M1) of the formula:

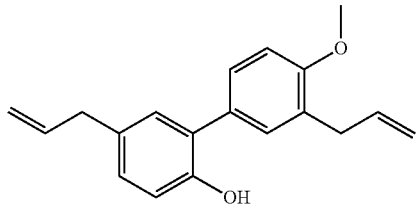

4'-O-methylhonokiol (MH)

While the present invention is exemplified by 4'-O-methylhonokiol as a CB2 receptor mixed-type agonist/inverse agonist, any CB2 receptor ligand, which exerts inverse agonistic effect on CB2 receptors at the level of cAMP production as determined in assays well known in the art (see herein above), is effective in treating ADHD/ADD and/or hyperactivity and/or a tic disorder, such as TS, and/or OCD in accordance with the teachings of the present invention.

In some embodiments, a CB2 receptor inverse agonist used to implement the teachings of the present invention is a selective estrogen receptor modulator (SERMs).

It is noted that SERMs have been shown to behave as CB2 receptor inverse agonists (see Kumar et al., Biochem. Biophys. Res. Commun. 435: 76-781, 2013; Prather et al., Biochem. Biophys. Res. Commun. 441: 339-343, 2013). An anecdotal report showed a therapeutic effect of the anti-estrogenic agent clomiphene citrate on a male patient with TS/OCD (Sandyk, R., et al., Postgrad Med J. 63: 510, 1987).

Thus, according to another aspect, the present invention provides a method for the treatment of a psychiatric disorder comprising administering to a subject in need of such treatment a pharmaceutical composition comprising a therapeutically effective amount of a CB2 receptor inverse agonist, wherein the CB2 receptor inverse agonist is a selective estrogen receptor modulator (SERM), and wherein the psychiatric disorder is ADHD and/or OCD.

According to some embodiments, the SERM is selected from the group consisting of raloxifene, bazedoxifen, lasofoxifene, tamoxifen, afimoxifene, arzoxifene, ormeloxifene, toremifene, ospemifene, analogs, derivatives or a combination thereof. According to further embodiments, the SERM is selected from the group consisting of raloxifene, bazedoxifen, lasofoxifene and tamoxifen.

According to some embodiments, the efficacy of SERM to treat certain psychiatric disorders does not involve modulation of plasma LH, FSH and/or LHRH levels. According to other embodiments, the efficacy of SERM to treat certain psychiatric disorders does not involve binding to estrogen receptors.

In an additional embodiment, the CB2 receptor inverse agonist is N-(benzo[1,3]dioxol-5-ylmethyl)-7-methoxy-2-oxo-8-pentyloxy-1,2-dihydroquinoline-3-carboxamide known as JTE 907.

In a further embodiment, the CB2 receptor inverse agonist is SR 144528 (CAS number 192703-06-3).

It is to be understood that the present invention excludes the compounds of general formula I for use in the treatment of OCD. In addition, the present invention excludes SERM for use in treating tic disorders including TS.

According to additional embodiments, the compounds of general formula I, and particularly M1, exert their curative/therapeutic effects in a subject suffering from ADHD/ADD and/or hyperactivity and/or a tic disorder via a mechanism other than the CB2 receptor signaling pathway.

In general, a particular ligand which binds to a particular receptor is said to have affinity for that receptor.

A measure of affinity is often determined using a binding assay, for example, a competition or displacement assay, in which a candidate ligand competes with, or displaces, a known (or reference) ligand with a known (or reference) affinity. Such assays yield an inhibition constant (Ki) for the candidate ligand. The Ki value is inversely proportional to the affinity of the candidate ligand for the receptor. Thus, a low Ki value signifies a high affinity. In general, a Ki value of 10 µM or less is considered to be a pharmaceutically meaningful affinity for the receptor, and indicates that the candidate compounds is in fact a ligand for that receptor.

Assays for determining cannabinoid receptor affinity are well known. For example, radio-ligand displacement assays using tissues that contain the CB2 receptor (spleen, CB2 transfected cell lines) are common. An example of suitable radio-labeled known ligand is tritium-labeled CP55940 (a CB1/CB2 receptor agonist).

According to some embodiments of the present invention, the CB2 inverse agonist has a CB2 receptor inhibition constant (Ki) of 10 µM or less. According to additional embodiments, the Ki is 1 µM or less; 500 nM or less; 100 nM or less; 50 nM or less; 25 nM or less; 10 nM or less; 5 nM or less; 2 nM or less; or 1 nM or less. Each possibility is a separate embodiment of the present invention.

According to other embodiments, the range of Ki is: from 0.01 nM to 10 µM; from 0.1 nM to 1 µM; from 0.1 nM to 500 nM; from 0.1 nM to 100 nM; from 1 nM to 100 nM; from 1 nM to 50 nM. Each possibility is a separate embodiment of the present invention.

According to the principles of the present invention, the CB2 receptor inverse agonists of the present invention are selective to CB2 receptors showing higher affinity to CB2 receptors than to CB1 receptors. It should be appreciated that the Ki value of a CB2 receptor inverse agonist of some embodiments of the present invention towards CB2 receptors as compared to CB1 receptors is at least 10 times lower, at least 20 times lower, at least 30 times lower, at least 40 times lower, at least 50 times lower, at least 100 times lower, at least 200 times lower, at least 300 times lower, at least 400 times lower, at least 500 times lower, at least 600 times lower, at least 700 times lower, at least 800 times lower, at least 900 times lower, or at least 1000 times lower. Each possibility is a separate embodiment of the present invention.

Pharmaceutical Compositions

The pharmaceutical compositions disclosed herein are administered and dosed in accordance with good medical practice, taking into account the clinical condition of the individual patient, the disease to be treated, the site and method of administration, scheduling of administration, patient age, sex, body weight and other factors known to medical practitioners.

The therapeutically effective dose can be determined by a person having ordinary skill in the art upon perusal of the disclosure according to known considerations. The dose is typically effective to achieve improvement according to an appropriate measure by a person having ordinary skill in the art, and in some embodiments includes, but is not limited to, improvement of the subject functioning and/or improvement or elimination of symptoms and other indicators.

The therapeutically effective dose of the CB2 receptor inverse agonist can range from about 0.4 mg/kg to about 10 mg/kg, such as, for example, from about 0.4 mg/kg to about 8 mg/kg, from about 0.4 mg/kg to about 6 mg/kg, from about 0.4 mg/kg to about 4 mg/kg, from about 0.4 mg/kg to about 2 mg/kg, from about 0.4 mg/kg to about 1.8 mg/kg, from about 0.4 mg/kg to about 1.6 mg/kg, from about 0.4 mg/kg to about 1.4 mg/kg, from about 0.4 mg/kg to about 1.2 mg/kg, from about 0.4 mg/kg to about 1 mg/kg, from about 0.4 mg/kg to about 0.8 mg/kg, from about 0.4 mg/kg to about 0.6 mg/kg or from about 0.4 mg/kg to about 0.5 mg/kg. Each possibility is a separate embodiment of the invention.

The average daily dose of the CB2 receptor inverse agonist for a human subject (such as a human child, weighing between about 10 kg and about 40 kg or a human adult, weighing between about 40 kg and about 120 kg) can be about 5 mg, about 10 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 200 mg, about 300 mg, about 400 mg, or about 500 mg. Each possibility is a different embodiment of the invention. Each possibility is a separate embodiment of the invention.

The CB2 receptor inverse agonist can be administered once per week, twice per week, 3 times per week, 4 times per week, 5 times per week, 6 times per week, once per day, twice per day or 3 times per day. Each possibility is a separate embodiment of the invention.

In one embodiment, the subject is a human. In another embodiment the human subject is a human child. In a further embodiment, the human subject is a human teenager. In a still further embodiment, the human subject is a human adult. In a further embodiment, the subject is an animal.

The pharmaceutical compositions of the present invention can be administered through any suitable route, such as orally or parenterally including intravenously, intraarterially, intramuscularly, intraperitoneally, subcutaneously, intranasally, vaginally, or rectally.

The pharmaceutical compositions of the present invention can be manufactured by any suitable method or combination of methods as known in the art with which a person having ordinary skill in the art is familiar and include conventional mixing, dissolving, granulating, dragee-making, levigating, emulsifying, encapsulating, entrapping or lyophilizing. The pharmaceutical compositions typically include a pharmaceutically acceptable carrier optionally comprising diluents, excipients or auxiliaries. Proper formulation can be done by a person having ordinary skill in the art with reference to standard procedures as disclosed, for example, in "Remington's Pharmaceutical Sciences," Mack Publishing Co., Easton, Pa., latest edition, which is incorporated herein by reference as if fully set forth herein.

For topical administration, the pharmaceutical compositions of the present invention can be formulated as solutions, gels, ointments, creams, suspensions, sprays, and the like as are well-known in the art.

Systemic formulations include those designed for administration by injection, e.g., subcutaneous, intravenous, intramuscular, intrathecal or intraperitoneal injection, as well as those designed for transdermal, transmucosal, inhalation, oral or pulmonary administration.

For injection, the pharmaceutical compositions of the present invention can be formulated in aqueous solutions, preferably in physiologically compatible buffers such as Hanks's solution, Ringer's solution, or physiological saline buffer. The solution may contain formulatory agents such as suspending, stabilizing and/or dispersing agents.

Alternatively, the pharmaceutical composition can be in powder form for reconstitution with a suitable vehicle, e.g., sterile pyrogen-free water, before use.

For transmucosal administration, penetrants appropriate to the barrier to be permeated can be used in the composition. Such penetrants are generally known in the art.

For oral administration, the pharmaceutical compositions of the present invention can be readily formulated by combining a selected CB2 receptor inverse agonist with pharmaceutically acceptable carriers well known in the art. Such carriers enable the composition to be formulated as tablets, pills, dragees, capsules, liquids, gels, syrups, slurries, suspensions, sprays, and the like, for oral ingestion by a patient to be treated. For oral solid formulations such as, for example, powders, capsules and tablets, suitable excipients include fillers such as sugars, e.g., lactose, sucrose, mannitol and sorbitol; cellulose preparations such as maize starch, wheat starch, rice starch, potato starch, gelatin, gum tragacanth, methyl cellulose, hydroxyprop ylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms can be sugar-coated or enteric-coated using standard techniques.

For oral liquid compositions such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the composition can take the form of tablets, lozenges, sprays, and the like, formulated in conventional manner.

For administration by inhalation, the pharmaceutical compositions of the present invention can be delivered in the form of an aerosol spray from pressurized packs or a nebulizer, with the use of a suitable propellant, e.g., dichlorodifluoromethane, trichloroiluoromethane, dichloro-tetrafluoro-ethane or carbon dioxide. In the case of a pressurized aerosol, the dosage unit may be determined by providing a valve to deliver a metered amount. Capsules and cartridges of gelatin for use in an inhaler or insufflator may be formulated containing a powder mix of the composition and a suitable powder base such as lactose or starch.

The pharmaceutical compositions of the present invention can be formulated for rectal or vaginal administration such as suppositories or retention enemas, e.g., containing conventional suppository bases such as cocoa butter or other glycerides.

The pharmaceutical compositions of the present invention can be formulated as long-acting depot formulations. Such long acting compositions may be administered by implantation (for example subcutaneously or intramuscularly) or by intramuscular injection. Thus, for example, the composition may be formulated as a depot preparation with suitable polymeric or hydrophobic materials (for example as emulsion in acceptable oil) or ion exchange resins, or as sparingly soluble derivatives, for example, as a sparingly soluble salt. For example, a composition may comprise a sustained-release system, such as semipermeable matrices of solid polymers containing the CB2 inverse agonist. Various sustained-release materials have been established and are well known by those skilled in the art. Sustained-release capsules may, depending on their chemical nature, release the composition for a few weeks up to over 100 days.

Due to their hydrophobic nature, the compounds of the present invention are readily dissolved in lipids. In some embodiments, other pharmaceutical delivery systems, such as compositions including liposomes or nanoparticles as known in the art, can be employed for implementing the teaching of the present invention.

In some embodiments, the CB2 receptor inverse agonist such as M1 or SERM can be co-administered with an additional active pharmaceutical ingredient, for example an additional active pharmaceutical ingredient for the treatment of a psychiatric disorder, either via a single dosage form (making up the same composition) or by separate administration of each active pharmaceutical ingredient, wherein the separate administration is sequential or concurrent.

EXAMPLES

Materials

The CB2 receptor agonist HU-308 (PNAS 1999, 96(25): 14228-14233) was purchased from Tocris. The inverse agonist CB2 receptor ligand 4-O-methylhonokiol designated herein below M1 was provided by Prof Gertsch, University of Bern, Switzerland (Schuehly et al., Chem. & Biol. 18:1053-64, 2011).

Cremophor EL and chemicals were purchased from Sigma-Aldrich, St. Louis, Mo., USA.

CB2 receptor agonist solutions were prepared as follows: Beta-caryophyllene designated herein below CB2 agonist2 in cremophor EL/ethanol/saline (1:0.6:18); or HU-308 in cremophor EL/ethanol/saline (1:0.6:18) or in cremophor EL/DMSO/saline (1:0.6:18).

The solution of 4-O-methylhonokiol (M1) was also prepared in cremophor EL/ethanol/saline (1:0.6:18) or in cremophor EL/DMSO/saline.

Mice Models

For the treated mice, one of the two CB2 receptor-selective agonist solutions: either CB2 agonist2 solution or H-308 solution, was administered by intravenous administration to mice pups to induce ADHD-like behavior and/or obsessive-compulsive-like behavior as a murine model for ADHD and OCD. The CB2 agonist solution was injected every other day on postnatal days 1-5 or 3-15 (7-8 administrations total) or every day on postnatal days 1-5 (5 administrations total), for a total dose of 0.5, 5 or 10 mg/kg CB2 agonist2 or 5 mg/kg HU-308. In order to test the effect of non-agonist or mixed-type agonist/inverse agonist CB2 receptor ligands on hyperactivity, the effects of M1 were studied.

For the control group, mice pups were injected intravenously with an equivalent amount of the vehicle cremophor EL/ethanol/saline (1:0.6:18) according to the above schedule.

Assessment of AMID-Like Behavior:

Open-Field Test (Crossing and Rearing, Defecation, Grooming)

Mice were assessed for hyperactive behavior on postnatal days 16-20, 26-39, at age 13 weeks and at age 23 weeks. Mice were placed in the center of a transparent glass cage 30×40×31 cm divided into squares of 7.5×7.5 cm. The number of squares crossed and the rearing activity were evaluated for 8 min.

Attention Test: Prepulse Inhibition (PPI) of the Startle Reflex

A weak audible stimulus (74-90 dB tone) "prepulse" was used to inhibit the acoustic startle response to a subsequent strong audible stimulus (120 dB tone) "pulse". Reduced prepulse inhibition of the startle reflex (PPI) was taken as an index of the positive symptoms of deficits in attention.

PPI was assessed similarly to the method described by Varty et al. (2001). Mice were placed in a startle chamber and allowed to acclimatize for 5 minutes A loudspeaker produced startling "pulse" at 120 dB and thereafter 65 dB background white noise or one of six 20 ms duration "prepulses" at 74, 78, 82, 86, and 90 dB followed after 20 ms by a 40 ms startling "pulse" at 120 dB. The response of each mouse was recorded and stored by a computer. Each test session lasted for 11 minutes and consisted of 5 presentations of each of the prepulse/pulse sound stimuli (total of 30 or 35) presented in random order and separated by 15 second intervals. The magnitude of prepulse inhibition was calculated as percentage PPI=[1-(acoustic startle for prepulse+pulse)/(acoustic startle for pulse alone)]×100.

Impulsivity

Four groups of mice were defined:
Group 1: control mice treated with the vehicle at the age of 13 weeks;
Group 2: control mice treated with the M1 solution (5 mg/kg) at the age of 13 weeks;
Group 3: model mice (10 mg/kg CB2 agonist2) treated with the vehicle at the age of 13 weeks; and
Group 4: model mice (10 mg/kg CB2 agonist2) treated with the M1 solution (5 mg/kg) at the age of 13 weeks.

The treatment consisted of a single intravenous administration of the vehicle or the M1 solution Impulsivity was tested 24 hours after treatment.

Impulsivity as measured by the paucity of time spent on the two anxiety-provoking, open arms (as opposed to the two enclosed arms) of an "Elevated Plus Maze" was used as a parameter of negative symptoms of schizophrenia (Josselyn and Vaccarino, 1998). The plus maze was elevated 50 cm above the table top. Behavior of each mouse was recorded for 5 minutes by a video camera and scored using the "EthoVision" software (Noldus), measuring the number of entries as well as the amount of time spent in each arm, open or closed. Reduced time spent in the closed arms indicated reduced anxiety. Increased time spent in the opened arms indicated increased risk behavior (hyperactive and impulsive).

Assessment of Tourette's Syndrome-Like Behavior (Vocal and Motor Tics):

Vocal Tics

Mice were recorded at the age of 13 or 23-25 weeks with an ultrasonic voice recorder (Noldus). Mice were recorded at the age of 29 days with an ultrasonic voice recorder (AviSoft). Single mice were recorded in a cage for 10 min (according to sex and type of treatment). The number and duration of events at 20-40 kHz and at 50-70 kHz were analyzed. In some experiments, 24 h following M1 treatment, each mouse was recorded for 10 min before and after stress. Stress was induced by incubation for 10-15 min in a mouse restrainer.

Motor Tics

Mice were assessed for hyperactive behavior on postnatal days 16-20 or 29, or at the age of 13 weeks with the open field test (as above). The number of jumps was recorded and counted manually.

Example 1: Model Mice Behavior

Figure 1B:
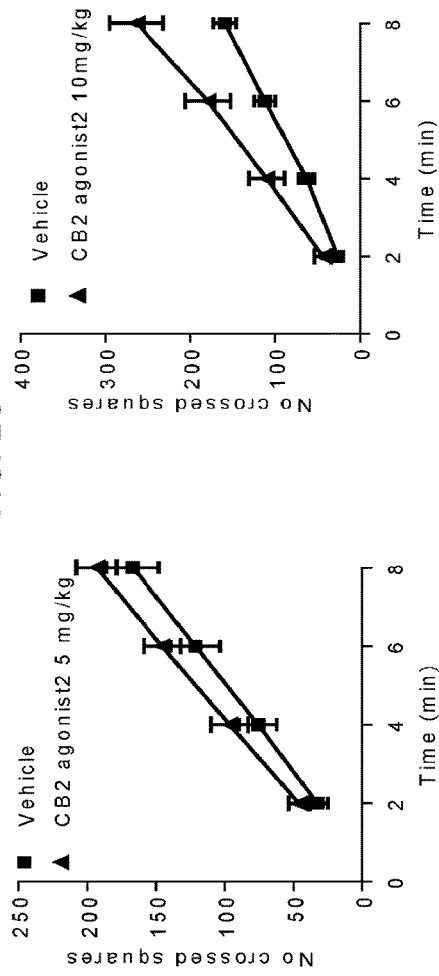
Figure 1C:
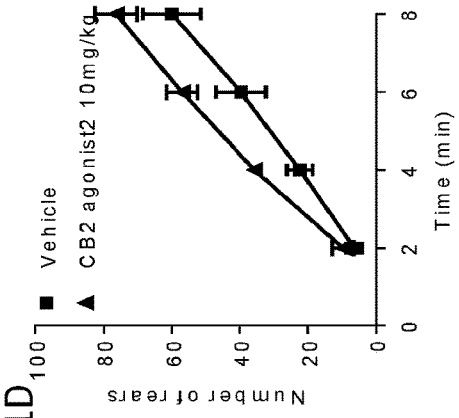
Figure 1D:
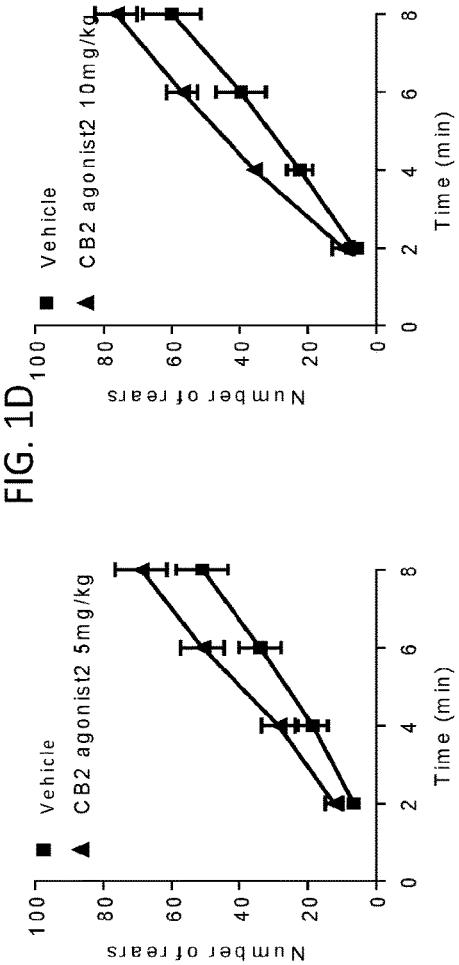

FIGS. 1A and 1B show increased ambulation (FIG. 1A) and rearing (FIG. 1B) using the open field test at postnatal days 16-19 following administration of 5 mg/kg CB2 agonist2 at postnatal days 5-13. FIGS. 1C and 1D show increased ambulation (FIG. 1C) and rearing (FIG. 1D) using the open field test at postnatal days 16-19 following administration of 10 mg/kg CB2 agonist2 at postnatal days 5-13.

Figure 2A:
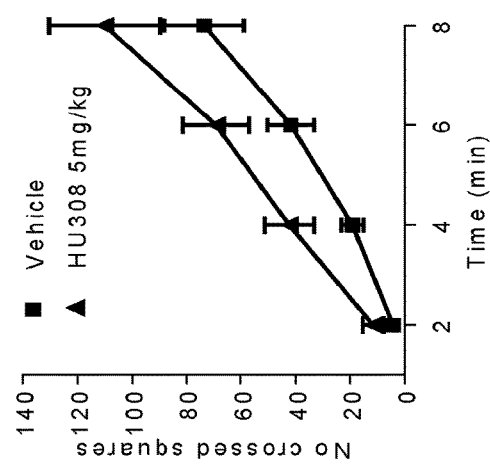
FIGS. 2A-B are line graphs showing the effect of postnatal administration of HU-308 on ambulation (FIG. 2A) and rearing (FIG. 2B) using the open field test.
Figure 2B:
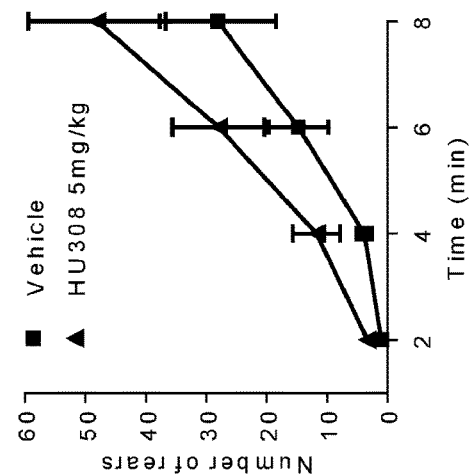

FIGS. 2A and 2B show increased ambulation (FIG. 2A) and rearing (FIG. 2B) using the open field test at postnatal days 16-19 following administration of 5 mg/kg HU-308 at postnatal days 5-13. These results suggest that postnatal administration of the cannabinoid CB2 receptor agonists, e.g., CB2 agonist2 or HU-308, induce symptoms of hyperactivity at postnatal days 16-19.

Figure 3A:
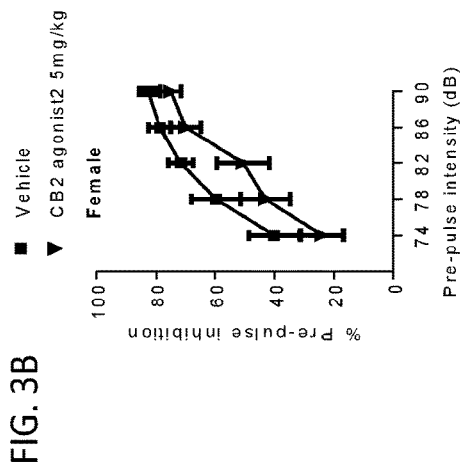
FIGS. 3A-D show the effect of postnatal administration of CB2 agonist2 on the response to acoustic startle or pre-pulse inhibition.
Figure 3B:
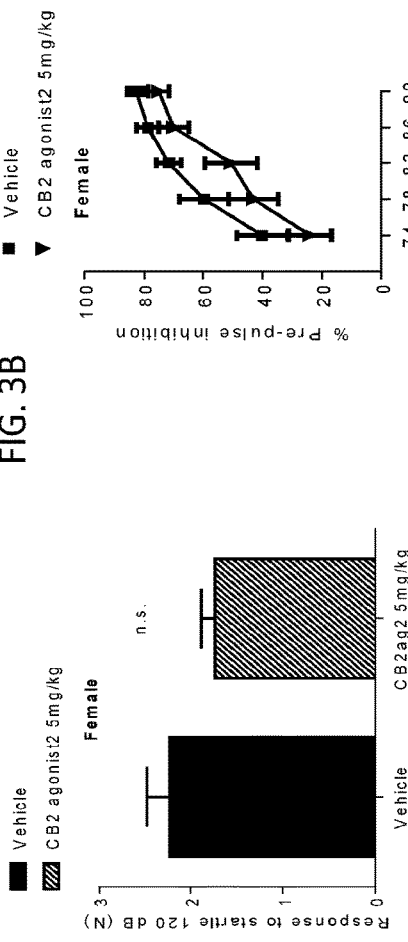
Figure 3C:
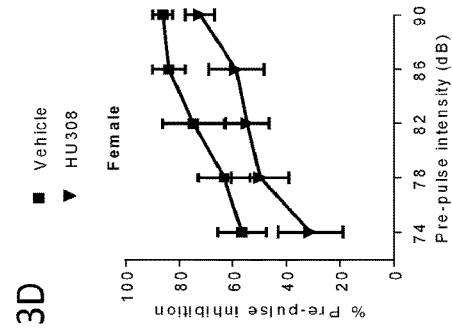
Figure 3D:
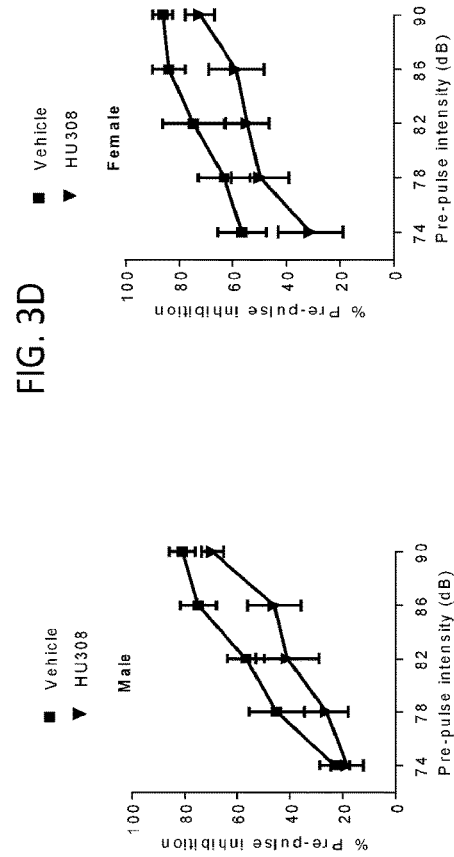

FIG. 3A shows that the acoustic startle between model mice and control mice was not significantly different at the age of 8 weeks. FIG. 3B shows decreased percent pre-pulse inhibition in model female mice, i.e., female mice treated with CB2 agonist2 at postnatal days 5-13, indicating a lower attention level. FIGS. 3C and 3D show decreased percent pre-pulse inhibition in male mice (FIG. 3C) or in female mice (FIG. 3D) injected with HU-308 at postnatal days 5-13, indicating lower attention levels.

Example 2: Effect of M1 on Grooming Behavior and Feces Secretion

Figure 4A:
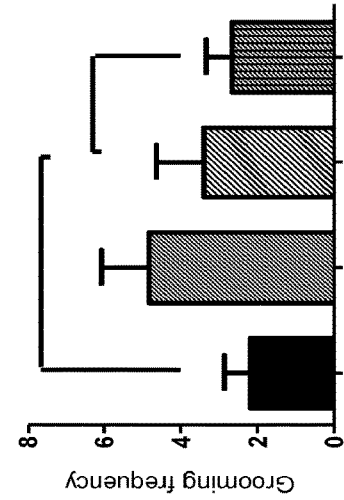
FIGS. 4A-C are bar graphs showing the effect of treatment with M1 on CB2 agonist2-induced grooming duration (FIG. 4A), and grooming frequency (FIG. 4B), and on CB2 agonist2-reduced feces secretion (FIG. 4C).
Figure 4B:
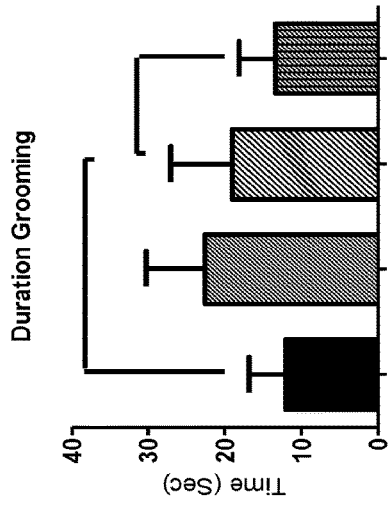
Figure 4C:
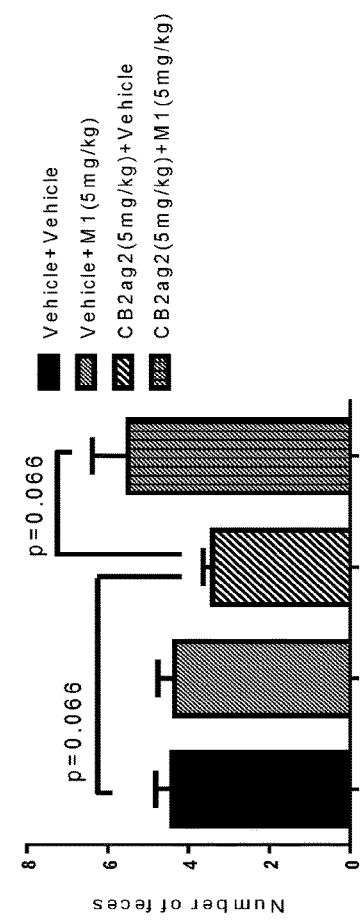

To study the effect of the M1 composition on OCD-like induced grooming behavior, mice were injected with the vehicle or with CB2 agonist2 on postnatal days 5-13 and then treated at the age of 23 weeks with either a vehicle or M1 as follows:
Group 1: control mice treated with the vehicle at the age of 23 weeks;
Group 2: control mice treated with the M1 solution (5 mg/kg) at the age of 23 weeks;
Group 3: model mice (5 mg/kg CB2 agonist2), treated with the vehicle at the age of 23 weeks; and
Group 4: model mice (5 mg/kg CB2 agonist2), treated with the M1 solution (5 mg/kg) at the age of 23 weeks.
The treatment consisted of a single i.p. administration of the vehicle or the M1 solution. Grooming behavior was tested 48 hours after treatment.
The effects of M1 on grooming behavior are shown in FIGS. 4A and 4B. Model mice showed increased grooming duration and frequency, indicating OCD-like behavior, which was reversed by administration of the M1 solution.
The effects of M1 on feces secretion are shown in FIG. 4C. Model mice showed decreased secretion of feces, which was reversed by administration of the M1 composition.

Example 3: Effect of M1 on Ambulation and Rearing

Figure 5A:
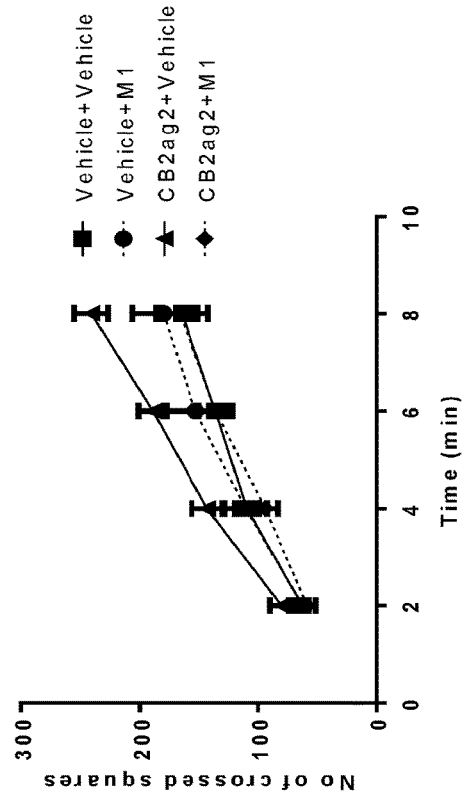
FIGS. 5A-B are line graphs showing the effect of treatment with M1 on CB2 agonist2-induced ambulatory behavior (FIG. 5A) and rearing (FIG. 5B).
Figure 5B:
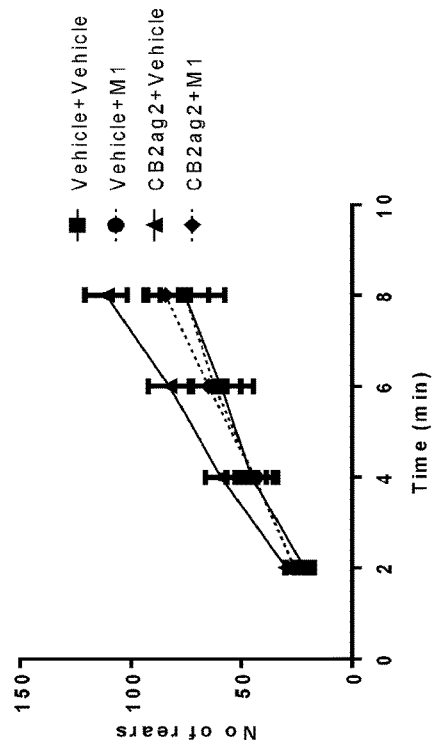

To study the effect of M1 on increased ambulation and rearing, a hyperactivity-like behavior, mice were injected with vehicle or CB2 agonist2 on postnatal days 1-5 and then treated at the age of 13 weeks with vehicle or M1 (5 mg/kg) as follows:
Group 1: control mice treated with the vehicle at the age of 13 weeks;
Group 2: control mice treated with the M1 solution (5 mg/kg) at the age of 13 weeks;
Group 3: model mice (5 mg/kg CB2 agonist2), treated with the vehicle at the age of 13 weeks; and
Group 4: model mice (5 mg/kg CB2 agonist2), treated with the M1 solution (5 mg/kg) at the age of 13 weeks.
The treatment consisted of a single i.p. administration of the vehicle or the M1 solution. Ambulation and rearing were evaluated 30 minutes after treatment in the open field test.
As shown in FIGS. 5A and 5B, CB2 agonist2 was shown to increase ambulation (FIG. 5A) and rearing (FIG. 5B), which were reversed by administration of the M1 solution.

Example 4: Impulsive/Hyperactive Behavior

Figure 6A:
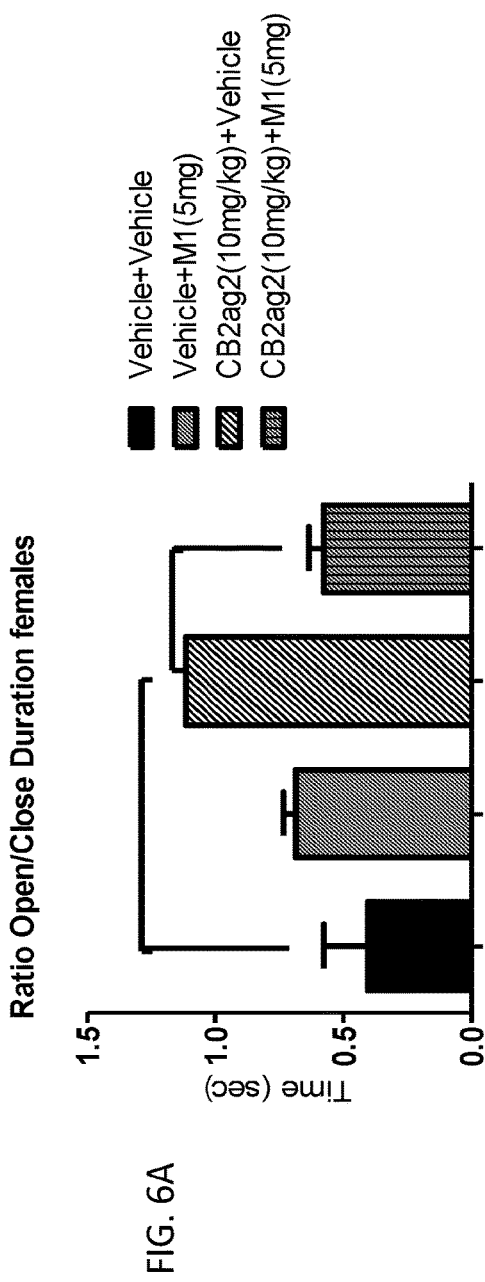
FIGS. 6A-B are bar graphs showing the effect of treatment with M1 on CB2 agonist2-induced impulsive/hyperactive behavior as measured by open/close duration time in female mice (FIG. 6A) and by open/close frequency in male+female mice (FIG. 6B).
Figure 6B:
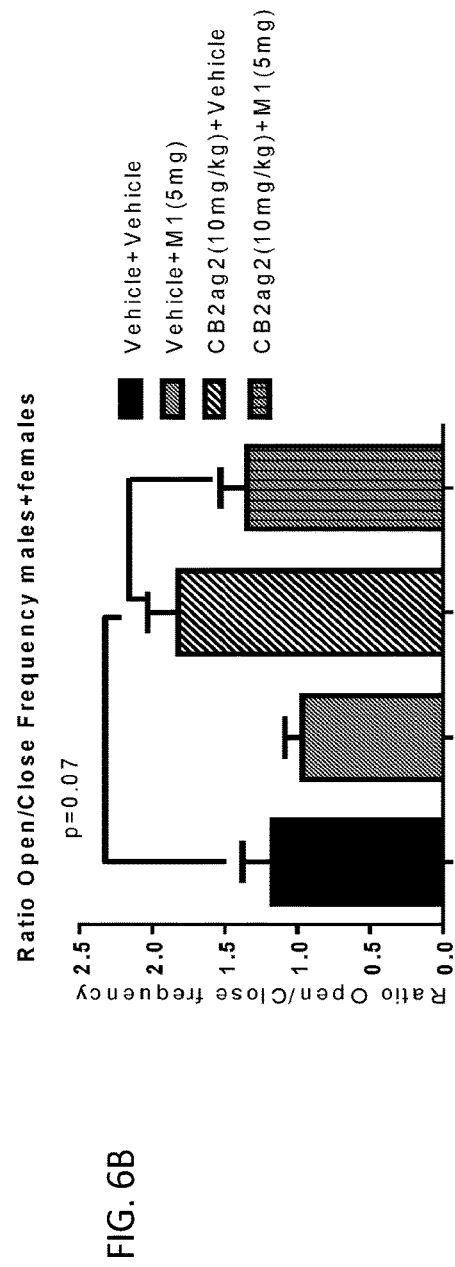

To study the effect of M1 on impulsive/hyperactive behavior, mice were injected with vehicle or CB2 agonist2 on postnatal days 1-5 and then treated at the age of 13 weeks with vehicle or M1 (5 mg/kg) as follows:
Group 1: control mice treated with the vehicle at the age of 13 weeks;
Group 2: control mice treated with the M1 solution (5 mg/kg) at the age of 13 weeks;

Group 3: model mice (5 mg/kg CB2 agonist2), treated with the vehicle at the age of 13 weeks; and
Group 4: model mice (5 mg/kg CB2 agonist2), treated with the M1 solution (5 mg/kg) at the age of 13 weeks.
The treatment consisted of a single i.p. administration of the vehicle or the M1 solution. The duration ratio open arm/close arm and the frequency ratio open arm/close arm in the Elevated Plus Maze were evaluated 24 hours after treatment with either vehicle or M1.
FIGS. 6A and 6B show that postnatal administration of CB2 agonist2 increased the ratio of duration in the open arm/close arm measured in the Elevated Plus-Maze test in females (FIG. 6A) and in males+females (FIG. 6B) at the age of 13 weeks. These results indicate an increased impulsive/hyperactive behavior at adulthood. M1 administered 24 hours before the test reversed this behavior.

Example 5: Tourette's Syndrome-Like Behavior: Vocal and Motor Tics

Table 1 shows that postnatal administration of HU-308 (5 mg/kg) during postnatal days 5-13 induced abnormal motor tics/head twitches at the age of 12 weeks as measured in the open field test.

TABLE 1

| Motor tics induced by HU-308. |||
| --- | --- | --- |
| Recorded time (seconds) | Number of tics | Direction of tic |
| 17 | 1 | head movement (left-right) |
| 21 | 2 | leg (rear) movements |
| 24 | 1 | head movement (left-right) |
| 43 | 2 | head movement (left-right) |
| 45 | 2 | jumping |
| 80 | 5 | change direction |
| 83 | 2 | sniffing and jumping back |
| 85 | 1 | sniffing and jumping back |
| 88 | 1 | jumping |
| 90 | 1 | head movement (all directions) |
| Total | 18 | |

Figure 8A:
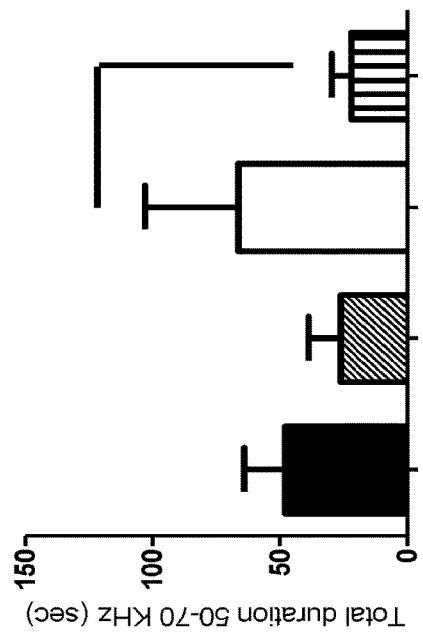
FIG. 8AC are bar graphs showing the effect of treatment with M1 on CB2 agonist2-induced vocal tics/events in female mice at 50-70 kHz, after stress.
Figure 8B:
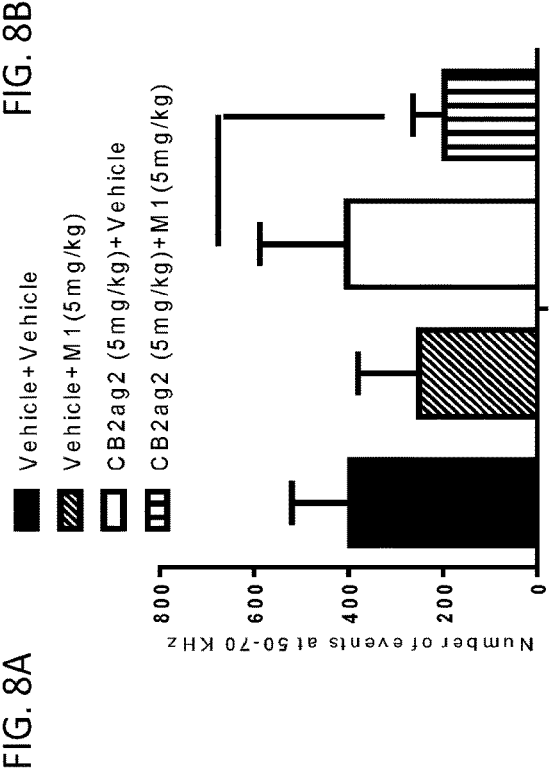
FIG. 8B shows the effect of CB2 agonist2 and M1 on the total duration of vocal events.
Figure 8C:
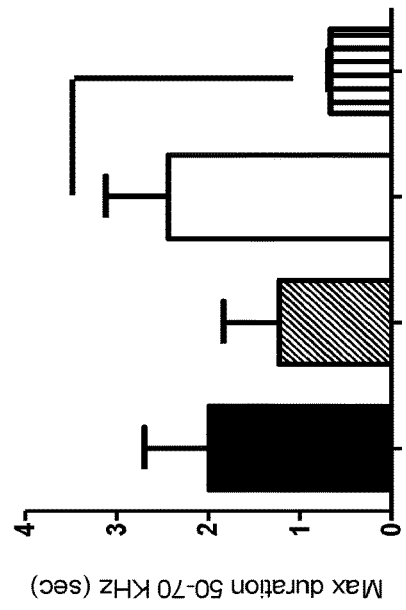
FIG. 8C shows the effect of CB2 agonist2 and M1 on maximum duration of the vocal events.
Figure 9A:
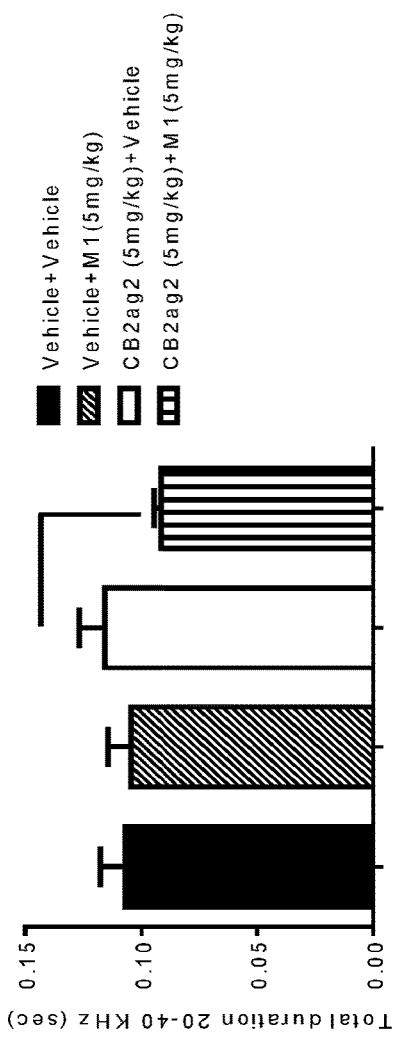
FIGS. 9A-B are bar graphs showing the effect of treatment with M1 on CB2 agonist2-induced vocal tics/events in unstressed male mice at 20-40 kHz.
Figure 9B:
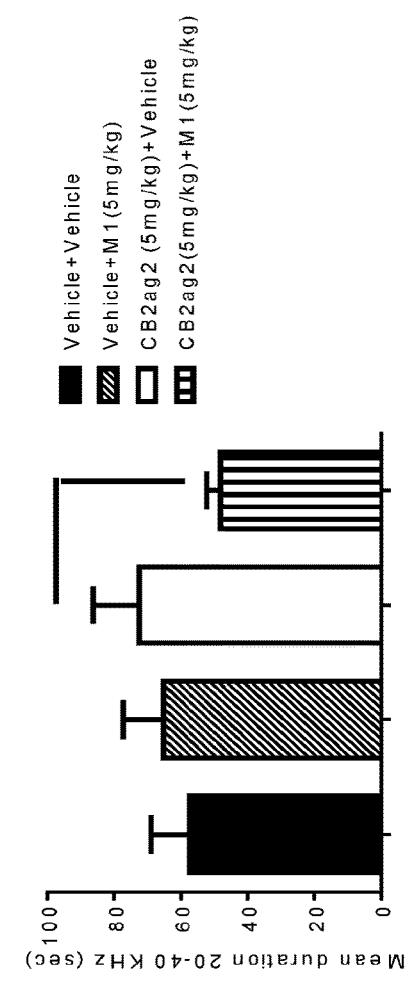
Figure 10A:
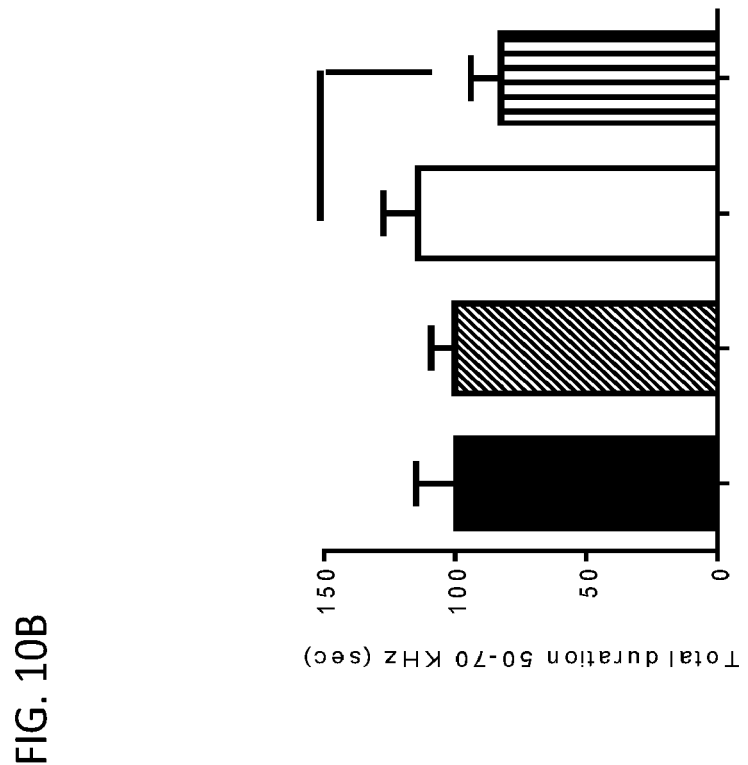
FIGS. 10A-B are bar graphs showing the effect of treatment with M1 on CB2 agonist2-induced vocal tics/events in unstressed male mice at 50-70 kHz.
Figure 10B:
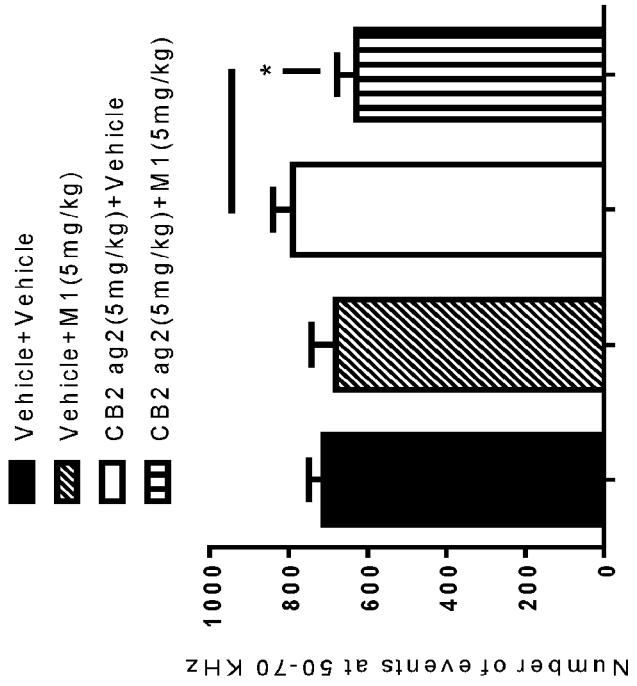

FIGS. 7A-C show that administration of CB2 agonist2 (5 mg/kg) during postnatal days 5-13 increased the number (FIG. 7A), total duration (FIG. 7B), and mean duration (FIG. 7C) of vocal events in female mice at the age of 23-25 weeks subjected to 20-40 KHz and stress. M1 reversed the effects of CB2 agonist2.
FIGS. 8A-C show that administration of CB2 agonist2 (5 mg/kg) during postnatal days 5-13 increased the number (FIG. 8A), total duration (FIG. 8B), and mean duration (FIG. 8C) of vocal events in female mice at the age of 23-25 weeks subjected to 50-70 KHz and stress. M1 reversed the effects of CB2 agonist2.
FIGS. 9A-B show that administration of CB2 agonist2 (5 mg/kg) during postnatal days 5-13 increased the total duration (FIG. 9A) and mean duration (FIG. 9B) of vocal events in male mice at the age of 23-25 weeks subjected to 20-40 KHz (before stress). M1 reversed the effects of CB2 agonist2.
FIGS. 10A-B show that administration of CB2 agonist2 (5 mg/kg) during postnatal days 5-13 increased the total duration (FIG. 10A) and mean duration (FIG. 10B) of vocal events in male mice at the age of 23-25 weeks subjected to 50-70 KHz (before stress). M1 reversed the effects of CB2 agonist2.

FIGS. 11A and 11C show that administration of CB2 agonist2 (0.5 mg/kg) at the age of 3-15 days increased ambulation and rearing as measured on day 26 in unstressed females. FIGS. 11B and 11D show that injection of M1 on day 29 reversed the effect of CB2 agonist2 on ambulation and rearing as measured on the same day in stressed females.

Figure 12A:
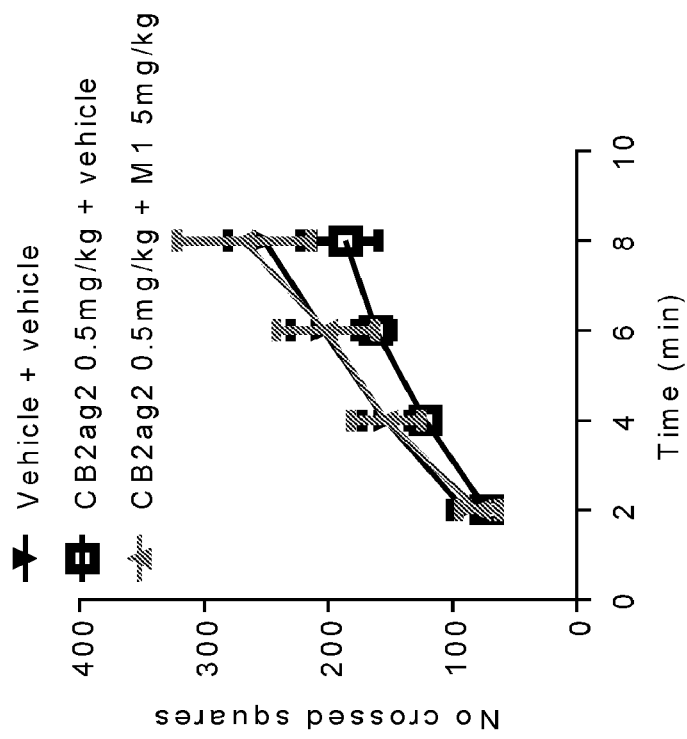
FIGS. 12A-B are bar graphs showing that treatment with M1 reversed the effect of 0.5 mg/kg CB2 agonist2 on rearing (FIG. 12A) and ambulation (FIG. 12B) at postnatal day 39.
Figure 12B:
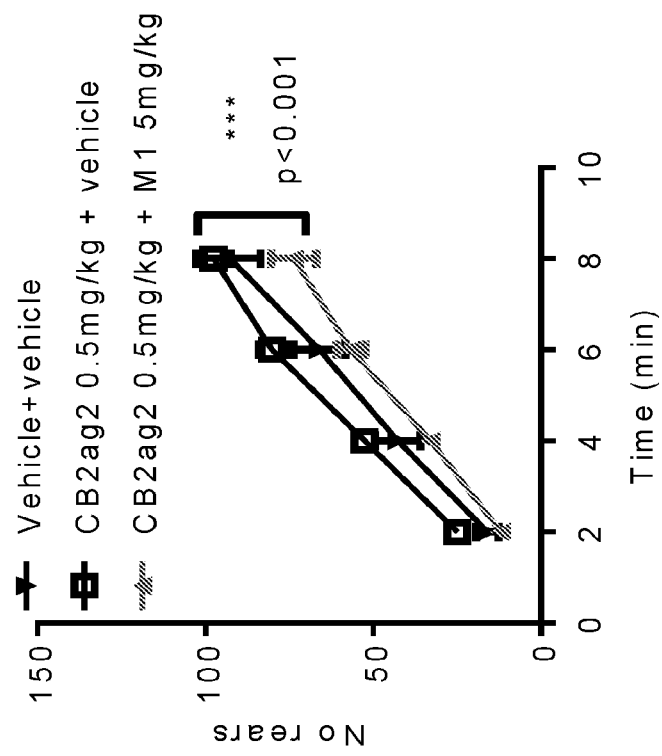

FIG. 12A shows that administration of CB2 agonist2 (0.5 mg/kg) at the age of 3-15 days increased rearing measured on day 36 in unstressed female mice (FIG. 12A). Injection of M1 on day 29 reversed the effect of CB2 agonist2 on rearing measured on day 36 before stress. FIG. 12B shows that administration of CB2 agonist2 (0.5 mg/kg) at the age of 3-15 days increased ambulation measured on day 39 in stressed female mice (FIG. 12A). Injection of M1 on day 29 reversed the effect of CB2 agonist2 on ambulation measured on day 39 after stress.

FIGS. 13A-B show that administration of CB2 agonist2 (0.5 mg/kg) at the age of 3-15 days increased grooming (FIG. 13A) and Feces secretion (FIG. 13B) measured on day 39 in stressed female mice. Injection of M1 (5 mg/kg) on day 29 reversed the effect of CB2 agonist2 on grooming (FIG. 13A) and feces secretion (FIG. 13B) measured on day 39 after stress.

FIGS. 13A-B show that administration of CB2 agonist2 (0.5 mg/kg) at the age of 3-15 days increased grooming (FIG. 13A) and feces secretion (FIG. 13B) measured on day 39 in stressed female mice. Injection of M1 (5 mg/kg) on day 29 reversed the effect of CB2 agonist2 on grooming (FIG. 13A) and on feces secretion (FIG. 13B) measured on day 39 after stress.

Figure 14A:
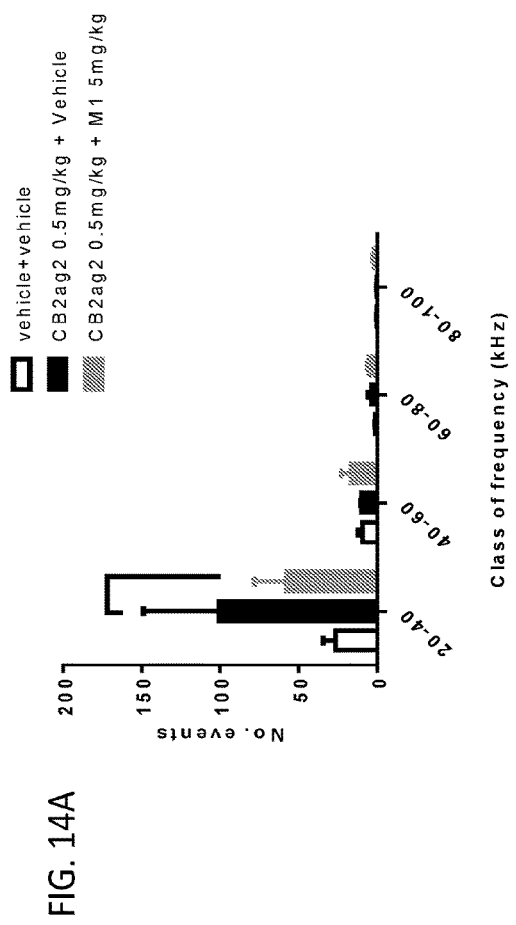
FIGS. 14A-B are bar graphs showing that M1 reversed the effect of 0.5 mg/kg CB2 receptor agonist2 on the number of vocal events (FIG. 14A) and the duration of vocal events (FIG. 14B) at 20-40 KHz frequency on postnatal day 29.
Figure 14B:
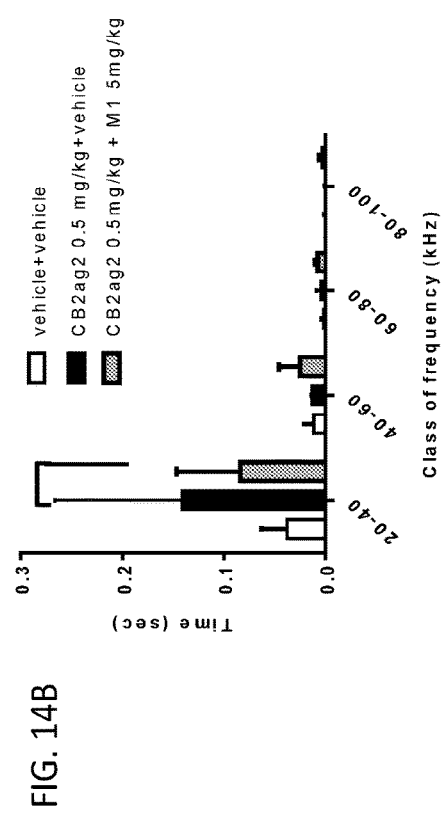

FIGS. 14A-B show that administration of CB2 agonist2 (0.5 mg/kg) at the age of 3-15 days increased the number of vocal events (FIG. 14A) and the duration of vocals (FIG. 14B) at frequency of 20-40 KHz measured on day 29 in female mice. Injection of M1 (5 mg/kg) on day 29 reversed the effect of CB2 agonist2 on the number of vocal events (FIG. 14A) and duration of vocals (FIG. 14B) measured on day 29.

Figure 15A:
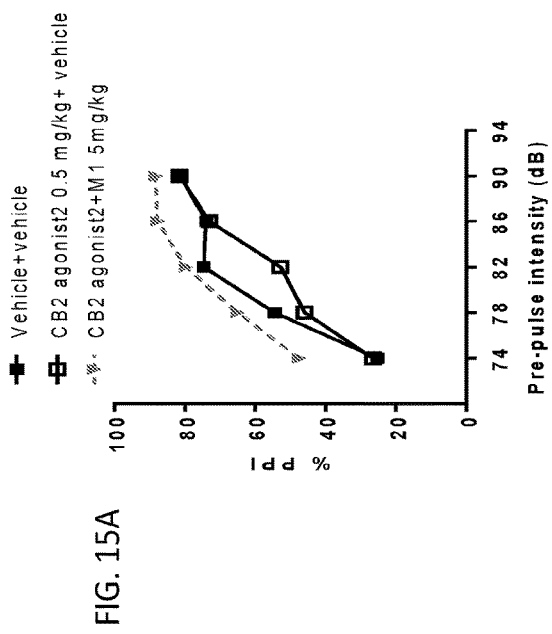
FIGS. 15A-B show the effect of M1 on prepulse inhibition (PPI) at postnatal day 100 (FIG. 15A), and response to prepulse tone (FIG. 15B) in vehicle or CB2 agonist 2 treated mice.
Figure 15B:
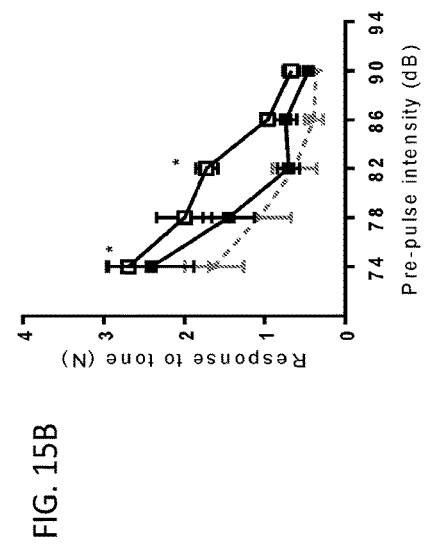

FIG. 15A shows that treatment with M1 reversed the effect of 0.5 mg/kg CB2 agonist2 on % PPI (pre-pulse inhibition) at postnatal day 100. FIG. 15B shows that treatment with M1 reversed the effect of 0.5 mg/kg CB2 agonist2 on the response to pre-pulse tone.

Figure 16A:
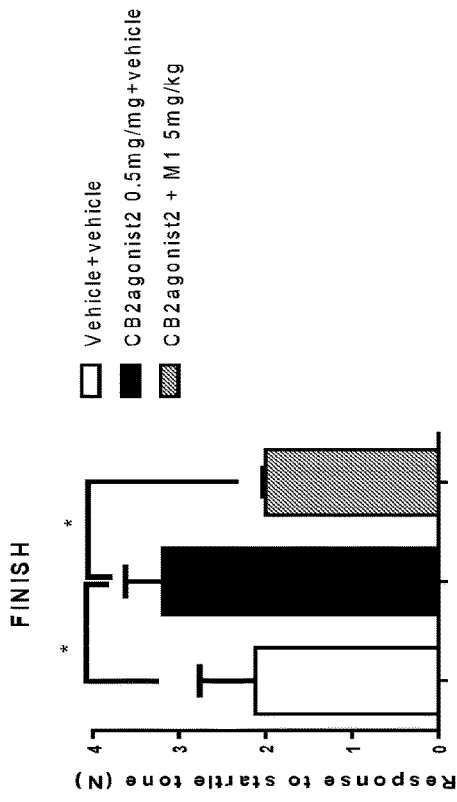
FIGS. 16A-C show the effect of M1 on the response to a startle tone of 120 dB at postnatal day 100 of mice treated with vehicle or CB2 agonist 2, at the start of the experiment (FIG. 16A) and at the end of the experiment (FIG. 16B).
Figure 16B:
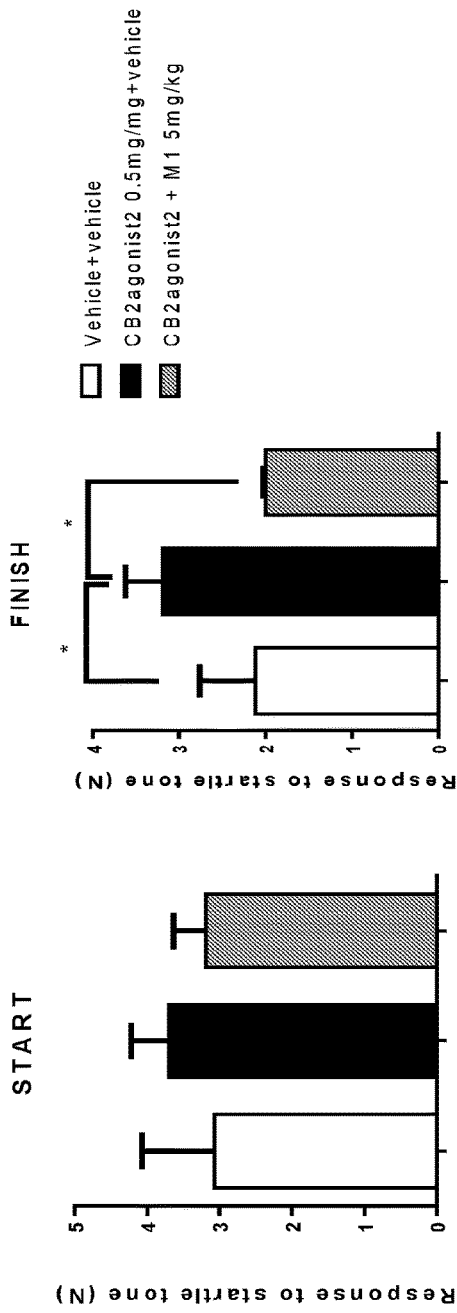
Figure 16C:
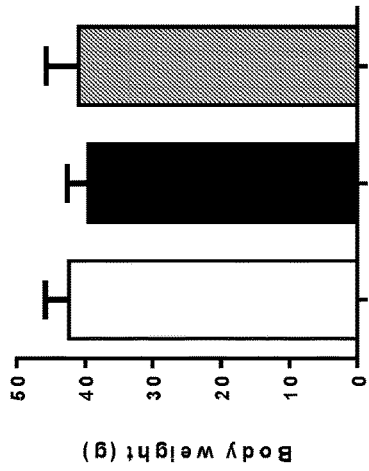

FIG. 16A shows that treatment with M1 had no effect on the response to the startle tone of 120 dB at postnatal day 100 in mice treated with 0.5 mg/kg CB2 agonist2 at the beginning of the experiment. FIG. 16B shows that treatment with M1 reversed the effect of 0.5 mg/kg CB2 agonist2 on the response to 120 dB that was re-evaluated at the end of the experiment. FIG. 16C shows that treatment with M1 had no effect on body weight at postnatal day 100 in mice treated with 0.5 mg/kg CB2 agonist2.

Figure 17B:
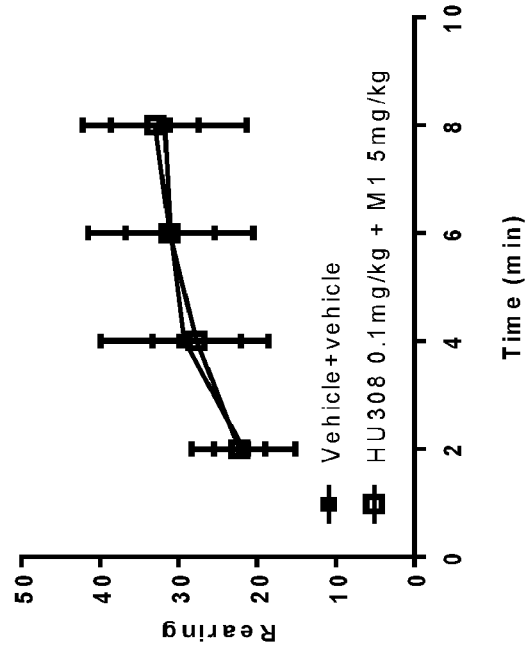
FIGS. 17A-B show that HU-308 induces hyperactivity at the age of 3 months (FIG. 17A) and that treatment with M1 reversed the effect of HU-308 on hyperactivity at that age.
Figure 17A:
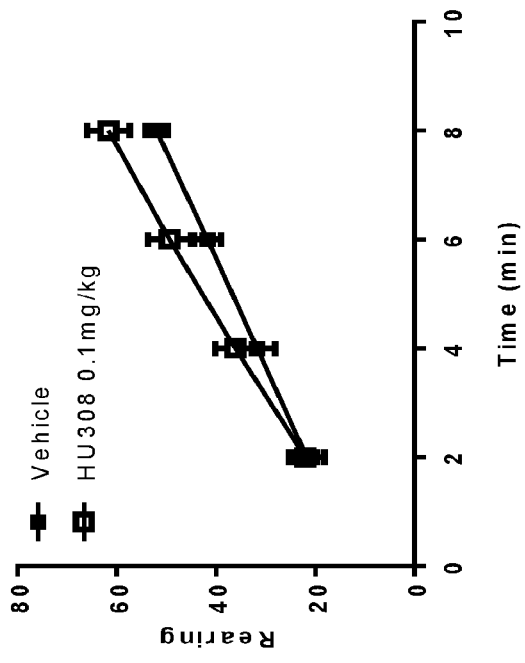

FIG. 17A shows that 0.1 mg/kg HU-308 induced hyperactivity at the age of 3 months. FIG. 17B shows that treatment with M1 reversed the effect of 0.1 mg/kg HU-308 on hyperactivity at the age of 3 months. M1 5 mg/kg was given to the treated group in gavage 30 minutes before the beginning of the experiment, suggesting it is orally available.

Example 6: Effect of SERM on Hyperactive Behavior

Hyperactive behavior in mice is induced by CB2 agonist2 or HU-308 as described in Example 1 herein above. Tamoxifene at a dose of 0.5 mg/kg up to a dose of 10 mg/kg is administered s.c. twice daily to the mice at the age of 25 days and the effect on ambulation and rearing is evaluated immediately thereafter as described in Example 1 herein above. Similarly, Tamoxifene at a dose of 0.5 mg/kg up to 10 mg/kg is administered i.p. twice daily to the mice at the age of 10 weeks, 13 weeks, or 25 weeks and the effect on ambulation and rearing is evaluated immediately thereafter as described in Example 1 herein above. Alternatively, tamoxifene is administered once either s.c. or i.p. one hour prior to evaluation of the hyperactive behavior.

The effect of raloxifene on the hyperactive behavior is evaluated using the same procedures as of tamoxifene.

It will be appreciated by persons skilled in the art that the present invention is not limited by what has been particularly shown and described herein above. Rather the scope of the invention is defined by the claims that follow.

The invention claimed is:

1. A method for treating vocal and/or motor tic behavior disorders comprising administering to a subject in need thereof a pharmaceutical composition comprising a therapeutically effective amount of a selective estrogen receptor modulator in a pharmaceutically acceptable carrier, wherein the selective estrogen receptor modulator is selected from the group consisting of raloxifene, bazedoxifene, lasofoxifene, tamoxifen, afimoxifene, arzoxifene, ormeloxifene, toremifene, ospemifene, and a combination thereof.

2. The method according to claim 1, wherein the selective estrogen receptor modulator is raloxifene.

3. The method according to claim 1, wherein the behavior disorder is Tourette syndrome.

4. The method according to claim 1 wherein the pharmaceutical composition is formulated in a dosage form selected from the group consisting of a solution, suspension, emulsion, powder, tablet, capsule, dragee, depot, granules, syrup, transdermal patch, spray, and suppository.

5. The method of claim 1 wherein the pharmaceutical composition is a solid dosage form.

6. The method of claim 5 wherein the solid dosage form is enteric-coated.

7. The method according to claim 1 wherein the pharmaceutical composition is formulated as an injectable solution and wherein the composition is administered as an intravenous injection, an intra-arterial injection, an intramuscular injection, an intradermal injection, an intraperitoneal injection, an intrathecal injection, a depot injection or a subcutaneous injection.

8. The method according to claim 1 wherein the pharmaceutical composition is formulated for oral, inhalation, transdermal, vaginal and or rectal administration routes.

9. The method of claim 1 wherein the therapeutically effective amount of the selective estrogen receptor modulator administered to the subject in need thereof ranges from about 0.4 mg/kg to about 10 mg/kg.

10. The method of claim 1 comprising administering an average daily dose of the selective estrogen receptor modulator ranging from about 5 mg to about 500 mg.

11. The method of claim 1 wherein the pharmaceutical composition comprising the therapeutically effective dose of the selective estrogen receptor modulator in a pharmaceutically effective carrier is administered to a human or non-human subject in need thereof once a week to 3 times per day.

12. A method for treating Tourette syndrome comprising administering to a subject in need thereof a pharmaceutical composition comprising a therapeutically effective amount of raloxifene in a pharmaceutically acceptable carrier.

* * * * *